(12) United States Patent
Bartzsch et al.

(10) Patent No.: US 11,393,654 B2
(45) Date of Patent: Jul. 19, 2022

(54) X-RAY MICRO-BEAM PRODUCTION AND HIGH BRILLIANCE X-RAY PRODUCTION

(71) Applicant: The Institute of Cancer Research: Royal Cancer Hospital, London (GB)

(72) Inventors: Stefan Bartzsch, London (GB); Uwe Oelfke, London (GB)

(73) Assignee: The Institute of Cancer Research: Royal Cancer Hospital, London (GB)

(*) Notice: Subject to any disclaimer, the term of this patent is extended or adjusted under 35 U.S.C. 154(b) by 545 days.

(21) Appl. No.: 16/308,780

(22) PCT Filed: Jun. 14, 2017

(86) PCT No.: PCT/GB2017/051733
§ 371 (c)(1),
(2) Date: Dec. 10, 2018

(87) PCT Pub. No.: WO2017/216555
PCT Pub. Date: Dec. 21, 2017

(65) Prior Publication Data
US 2019/0164717 A1    May 30, 2019

(30) Foreign Application Priority Data

Jun. 17, 2016 (GB) ...................... 1610646
Oct. 12, 2016 (GB) ...................... 1617330

(51) Int. Cl.
*H01J 35/00* (2006.01)
*H01J 35/26* (2006.01)
(Continued)

(52) U.S. Cl.
CPC ............... *H01J 35/26* (2013.01); *G21K 1/02* (2013.01); *G21K 1/087* (2013.01); *H01J 35/10* (2013.01); *H01J 35/14* (2013.01)

(58) Field of Classification Search
CPC .. H01J 35/10; H01J 35/14; H01J 35/26; H01J 2235/162
See application file for complete search history.

(56) References Cited

U.S. PATENT DOCUMENTS 3,689,790 A   9/1972 Haas et al.
4,045,672 A   8/1977 Watanabe
(Continued)

FOREIGN PATENT DOCUMENTS

EP   2075820   1/2009
EP   2775804   10/2014
(Continued)

OTHER PUBLICATIONS

Bräuer-Krisch E, et al (2015) Medical physics aspects of the synchrotron radiation therapies: Microbeam radiation therapy (MRT) and synchrotron stereotactic radiotherapy (SSRT). Phys Med 31: 568-583.
(Continued)

*Primary Examiner* — Dani Fox
(74) *Attorney, Agent, or Firm* — Rudy J. Ng; Bozicevic, Field & Francis LLP

(57) ABSTRACT

An x-ray micro-beam radiation production system is provided having: a source of accelerated electrons, an electron focusing component configured to focus the electrons provided by the source, and a target which produces x-rays when electrons impinge thereon from the source. The electron focusing component is configured to focus the electrons provided by the source such that they impinge at a focal spot having a width δ formed on a surface of the target. The focusing component is configured to move the electron beam relative to the target such that the focal spot moves across the target surface in the width direction, and/or the
(Continued)

target is movable relative to the focusing component such that the focal spot moves across the target surface in the width direction, the surface velocity of the focal spot across the target surface in the width direction being greater than $v_t$ where: formula (I), k, ρ and c denoting respectively the heat conductivity, the density and the heat capacity of the target material, and d denoting the electron penetration depth in the target material.

$$v_t = \frac{\pi k}{4\rho c} \cdot \frac{\delta}{d^2}, \quad (I)$$

14 Claims, 13 Drawing Sheets

(51) Int. Cl.
| | |
|---|---|
| *G21K 1/02* | (2006.01) |
| *G21K 1/087* | (2006.01) |
| *H01J 35/10* | (2006.01) |
| *H01J 35/14* | (2006.01) |

(56) References Cited

U.S. PATENT DOCUMENTS

| | | | |
|---|---|---|---|
| 4,426,722 A | 1/1984 | Fujimura | |
| 5,274,690 A | 12/1993 | Burke et al. | |
| 5,530,733 A | 6/1996 | Eggleston et al. | |
| 5,771,270 A * | 6/1998 | Archer | A61N 5/1042 378/150 |
| 2010/0329413 A1 | 12/2010 | Zhou et al. | |

FOREIGN PATENT DOCUMENTS

| | | |
|---|---|---|
| GB | 1604631 | 12/1981 |
| JP | 2016034373 | 3/2016 |

OTHER PUBLICATIONS

Crosbie et al., J. Synchrotron Rad. 22, 1035-5 1041 (2015).
Gelius U, et al (1984) A high resolution multipurpose ESCA instrument with X-ray monochromator. Nucl Instrum Methods Phys Res B1: 85-117.
Graves W, Brown W, Kaertner F, Moncton D. MIT inverse Compton souice concept. Nuclear Instruments and Methods in Physics Research Section A: Accelerators, Spectrometers, Detectors and Associated Equipment. 2009;608(1): S103-S5.
Huang Z. Brightness and coherence of synchrotron radiation and FELs. MOYCB101, Proceedings of IPAC2013, Shanghai, China. 2013.
Lengeler B, Schroer CG, Kuhlmann M, Benner B, Günzler TF, Kurapova O, et al. Refractive x-ray lenses. Journal of Physics D: Applied Physics. 2005;38(10A):A218.
Momose A. Phase-sensitive imaging and phase tomography using X-ray interferometers. Optics Express. 2003; 11(19):2303-14.
Oosterkamp W. Calculation of the Temperature Development in a Contact Heated in the Contact Surface, and Application to the Problem of the Temperature in a Sliding Contact. Journal of Applied Physics. 1948;19(12):1180-1.
Oppelt A, Kutschera W, Behner H, Bernhardt J, Neumeier E, Ponnath P, et al. Imaging systems for medical diagnostics. 2nd edition ed. Erlangen: Publicis MCD; 2005.
Pfeiffer F, et al (2006) Phase retrieval and differential phase-contrast imaging with low-brilliance X-ray sources. Nat Phys 2: 1-4.
Slatkin DN, et al (1992) Microbeam radiation therapy. Med Phys 19: 1395-1400.
Slides presented to EU SYRA3 COST (Cooperation in Science and Technology) work group on Mar. 15, 2016, Rostock, Germany.
Zeman et al. Radiation Res. 15 (1961), 496.
Hadsell et al "A first generation compact microbeam radiation therapy system based on carbon nanotube X-ray technology," Applied Physics Letter 103 183505-183505-5 (2013).

* cited by examiner

X-RAY MICRO-BEAM PRODUCTION AND HIGH BRILLIANCE X-RAY PRODUCTION

FIELD OF THE INVENTION

The present invention relates to the production of x-ray micro-beam radiation and to the production of high brilliance x-rays.

BACKGROUND

X-ray micro-beam radiation, i.e. x-ray radiation with a beam width in the order of microns, has been found to have a very limited effect on healthy living tissue at doses that, were they supplied by normal (i.e. macro-beam) radiation, would result in substantial tissue damage. Normal tissue can tolerate an x-ray micro-beam radiation dose in the order of thousands or even ten thousands of Grays. In contrast, cancerous tissue is more susceptible to x-ray micro-beam radiation. Accordingly, a distinct advantage of a treatment with x-ray micro-beam radiation is that healthy tissue surrounding the dosage site easily tolerates the radiation, and any collateral damage is rapidly repaired. Therefore, x-ray micro-beam radiation can be used as an effective form of radiotherapy to treat cancerous tissue.

In order to preserve the micro-beam structure in the tissue, short exposure times and parallel beams are required. Conventionally, in order to generate x-ray micro-beams with a sufficiently high dose rate, synchrotron radiation has been used. For example, facilities such as the European Synchrotron Radiation Facility (ESRF) in Grenoble, France, provide parallel x-ray beams with a dose rate of around 15,000 Gy/s and average photon energy of around 100 keV. However, such facilities are static complexes measuring many hundreds of meters in diameter, and therefore are clearly impractical for a widespread clinical application of micro-beam radiation therapy.

It would thus be desirable to be able to provide a system for generating x-ray micro-beams, which is significantly smaller, cheaper and less complex than a synchrotron.

Soft tissue contrast in conventional medical x-ray imaging based on tiny changes in the absorption coefficient is usually poor, phase contrast imaging, measuring the much larger relative differences in the refractive index, can provide significantly better contrast (Pfeiffer F, Weitkamp T, Bunk O, David C. *Phase retrieval and differential phase-contrast imaging with low-brilliance X-ray sources*. Nature physics. 2006; 2(4):258-61). Various methods have been used for phase contrast imaging (Momose A. *Phase-sensitive imaging and phase tomography using X-ray interferometers*. Optics Express. 2003; 11(19):2303-14), but all are based on the interferometric measurement of phase shifts induced by refractive index variations in the imaged object. The prerequisite to observe interference is the coherence of the radiation source. Whereas temporal coherence can be obtained with the aid of crystal monochromators, spatial coherence is much more delicate as path length differences between photons emitted from different parts of the x-ray source have to be much smaller than the wavelength $\lambda$ measuring in the order of only $10^{-11}$ m for hard x-rays. In order to achieve spatial coherence in conventional x-ray tubes, gratings have been proposed and used (Pfeiffer et al., ibid.) that absorb a substantial part of the initial x-ray beam intensity.

The beam quality of an x-ray source is usually characterised by its brilliance B, a quantity that measures the number of photons N emitted per time dt, area dA, emission angle interval $\Omega$ and frequency interval dv, $$B = \frac{dN}{dt \cdot d\Omega \cdot dA \cdot dv},$$

Due to beam divergence, broad photon energy spectra, large focal spot widths and a low electron to photon conversion efficiency, the radiation conventionally generated by x-ray tubes has only a low brilliance and is therefore unsuitable for applications such as phase contrast imaging, or other high resolution x-ray imaging.

X-ray radiation of high brilliance can be generated with synchrotrons. However, as discussed above, suitable synchrotrons are large, expensive facilities and are impractical for many applications especially in the medical field.

It would thus also be desirable to be able to provide a system for generating high brilliance x-rays, which is significantly smaller, cheaper and less complex than a synchrotron.

SUMMARY

In general terms, the present invention provides an x-ray radiation production system having:
  a source of accelerated electrons;
  an electron focusing component configured to focus the electrons provided by the source; and
  a target which produces x-rays when electrons impinge thereon from the source;
  wherein the electron focusing component is configured to focus the electrons provided by the source such that they impinge at a focal spot formed on a surface of the target.

In a first aspect the invention provides an x-ray micro-beam radiation production system having:
  a source of accelerated electrons;
  an electron focusing component configured to focus the electrons provided by the source;
  a target which produces x-rays when electrons impinge thereon from the source; and
  a collimator having one or more micro-beam forming apertures which collimate the produced x-rays into one or more respective micro-beams, the, or each, micro-beam forming aperture having a given shape on a cross-section therethrough perpendicular to the formed micro-beam;
  wherein the electron focusing component is configured to focus the electrons provided by the source such that they impinge at a focal spot formed on a surface of the target, the focal spot having substantially the same shape as a projection of the cross-sectional shape of the aperture(s) onto the target surface at the focal spot.

By focusing the electrons such that the focal spot has substantially the same shape as the projection of the cross-sectional shape of the, or each, micro-beam forming aperture, partial shadowing of the source along the micro-beam path behind the collimator can be avoided and the dose rate considerably increased. Moreover, in contrast to a micro-focus x-ray tube, the heat load can be spread over a larger area of the target, and the power of the source can hence be increased.

In a second aspect, the invention provides a method of operating the system of the first aspect having the steps of:
  providing electrons from the electron source;

focusing the electrons using the electron focusing component such that they impinge at the focal spot formed on the surface of the target, thereby producing x-rays; and collimating the resulting x-rays using the collimator thereby producing x-ray micro-beam radiation.

In general, the term micro-beam may be understood to mean a narrow beam of radiation with micrometre or sub-millimetre dimensions. Moreover, when there is more than one micro-beam, any two adjacent micro-beams may be substantially parallel.

Optional features of the invention, and particularly of the first and second aspects of the invention, will now be set out. These are applicable singly or in any combination with any suitable aspect of the invention.

The source may include an accelerator to accelerate the electrons. In this case, the target may be electrically neutral. However, alternatively or additionally, the target may be an anode to (further) accelerate the electrons.

The electron focusing component may be configured to focus the electrons provided by the source such that substantially all the focused electrons impinge on the focal spot of the target surface.

The target may be moveable relative to the focusing component such that the focal spot moves across the target surface. Additionally or alternatively, the focusing component may be configured to move the electron beam relative to the target such that the focal spot moves across the target surface. Either of these features may aid heat-dissipation through the target and may stop over-heating of the target at any particular point.

The target may be cylindrical, and the target may rotate around its axis to move the target relative to the focusing component. The target may rotate to provide a speed of movement of the focal spot over the target surface of at least 50 m/s, and preferably at least 100 or 150 m/s.

The electron source, the focusing component, and the target may be translated with a reciprocating motion (e.g. along the cylinder axis of a cylindrical target), and the focusing component may be configured to apply an equal but opposite reciprocating motion of the impingement position of the electrons on the target.

The, or each, aperture in the collimator may be a slit, and the focal spot may be correspondingly elongate in shape. In this case, the length direction of the slit(s) and the length direction of the focal spot can be parallel. This enables an even greater proportion of the x-ray radiation produced by the electrons impinging on the focal spot to be directed through the slit(s). More particularly, the slits may be rectangular in cross-section. When the target is cylindrical, the length direction of the focal spot can be parallel to the cylinder axis. The shortest dimension (the width) of the focal spot may be less than 1 mm, and preferably is less than 100 μm or less than 50 μm. The cross-section of the, or each, slit may have a width of at least 20 μm, and preferably the width is around 50 μm. The cross-section of the, or each, slit may have a width of at most 500 μm, and preferably at most 100 μm.

There may be plural apertures, and the centre-to-centre (ctc) distance between adjacent apertures may be at least 100 μm, and preferably at least 200 μm. The ctc distance may be at most 4000 μm, and preferably at most 800 μm.

The electrons may impinge on the target surface at a target angle, and the target angle may be controlled by the focusing component to be no more than 20° from the normal to the target surface at the focal spot. Preferably, the target angle may be no more than 10°.

The electrons may be accelerated with an acceleration voltage of at least 100 kV, preferably at least 400 kV, and most preferably at least 500 kV. The potential is typically limited by a high voltage supply and achievable electron currents.

The micro-beam radiation produced by the collimator may have a beam width of at least 20 μm, and preferably at least 50 μm. The beam width may be no more than 500 μm, and preferably no more than 100 μm.

The collimator may be spaced by a distance of at least 10 cm and/or at most 1 m from the focal spot.

The target may be made of tungsten or tungsten alloy. In some examples, the outer surface of the target may be formed of tungsten or a tungsten alloy and the core of the target is formed of copper. This can reduce weight and increase heat conduction. The outer surface of the target may have of a thickness of at least 5 mm and/or at most 10 mm.

The collimator may be at an angle to the normal to the target surface at the focal spot of at least 40° and/or at most 80°, e.g. an angle of around 60° may be suitable.

At a distance of 500 mm from the target, the micro-beam(s) formed by the collimator may deliver a radiation dose rate of at least 1 Gy/s. At a distance of 500 mm from the target, the micro-beam(s) formed by the collimator may deliver a radiation dose rate of no more than 1200 Gy/s. Herein, references to "dose" and "dose rate" refer to an entrance dose to water in 5 mm depth.

The x-rays collimated by the collimator may have a mean energy of at least 60 keV and/or at most 300 keV. The system may further have a filter (e.g. an aluminium or copper filter) between the target and the collimator. This can help to filter out low energy photons produced at the target by the impinging electrons.

In a third aspect, the present invention provides an x-ray radiation production system having:

a source of accelerated electrons;

an electron focusing component configured to focus the electrons provided by the source; and a target which produces x-rays when electrons impinge thereon from the source;

wherein the electron focusing component is configured to focus the electrons provided by the source such that they impinge at a focal spot having a width δ formed on a surface of the target; and wherein the focusing component is configured to move the electron beam relative to the target such that the focal spot moves across the target surface in the width direction, and/or the target is movable relative to the focusing component such that the focal spot moves across the target surface in the width direction, the surface velocity of the focal spot across the target surface in the width direction being greater than $v_t$, where:

$$v_t = \frac{\pi k}{4\rho c} \cdot \frac{\delta}{d^2},$$

k, ρ and c denoting respectively the heat conductivity, the density and the heat capacity of the target material, and d denoting the electron penetration depth in the target material.

In particular, for a given target and electron beam energy, by adopting a suitably small focal spot width δ and/or a suitably high surface velocity of the focal spot across the target surface $v_t$, a change in the physics of the target heating can be induced. This change enables higher electron beam intensities at the focal spot. The system can thus serve as a suitable and powerful compact x-ray source in phase contrast imaging and microbeam radiation therapy. The electron penetration depth d may be defined as $$E_{el} / \left\{ \left( \frac{\delta E_{el}}{\delta z}(z) \right) \max \right\},$$

where $E_{el}$ is the average kinetic energy absorption of an electron, $dE_{el}/dz(z)$ is the kinetic energy absorption per depth interval, and z is distance into the target from the surface.

In a fourth aspect, the invention provides a method of operating the system of the third aspect having the steps of:
providing electrons from the electron source;
focusing the electrons using the electron focusing component such that they impinge at a focal spot having a width δ formed on the surface of the target, thereby producing x-rays; and
moving the electron beam relative to the target such that the focal spot moves across the target surface in the width direction, and/or moving the target relative to the focusing component such that the focal spot moves across the target surface in the width direction, the surface velocity of the focal spot across the target surface in the width direction being greater than $v_t$ where:

$$v_t = \frac{\pi k}{4 \rho c} \cdot \frac{\delta}{d^2},$$

k, ρ and c denoting respectively the heat conductivity, the density and the heat capacity of the target material, and d denoting the electron penetration depth in the target material.

The system of the third aspect may be used to perform imaging, such as high resolution or phase contrast imaging. For example, a method of phase contrast imaging has the steps of: performing the method of the fourth aspect; and performing imaging using the produced x-rays as a source of illumination.

Optional features of the invention, and particularly of the third and fourth aspects of the invention, will now be set out. These are applicable singly or in any combination with any suitable aspect of the invention.

The source may include an accelerator to accelerate the electrons. In this case, the target may be electrically neutral. However, alternatively or additionally, the target may be an anode to (further) accelerate the electrons.

The electron focusing component may be configured to focus the electrons provided by the source such that substantially all the focused electrons impinge on the focal spot of the target surface.

The surface velocity of the focal spot across the target surface in the width direction may be at least two times greater than $v_t$.

The width δ of the focal spot may be less than 100 μm, and preferably is less than 10 μm or less than 1 μm.

The target may be cylindrical, and the target may rotate around its axis to move the target relative to the focusing component. The target may rotate to provide a surface velocity of at least 100 m/s, and preferably at least 200 or 500 m/s.

The electrons may impinge on the target surface at a target angle, and the target angle may be controlled by the focusing component to be no more than 20° from the normal to the target surface at the focal spot. Preferably, the target angle may be no more than 10°.

The electrons may be accelerated with an acceleration voltage of at least 40 kV.

Target materials may have spectral lines that enhance the beam brilliance at certain energies such as the Kα1 line of tungsten at 59.318 keV. Characteristic x-rays of a spectral line of the target material at around 60 keV may have a spatial coherence length of at least 5 μm at 1 m distance from the target, and preferably of at least 10 μm.

The produced characteristic x-rays of a spectral line of the target material at around 60 keV may have a photon flux of at least $1.10^6$ mm$^{-2}$ s$^{-1}$ at 1 m distance from the target, and preferably of at least $1.10^7$ mm$^{-2}$ s$^{-1}$ or at least $1.10^8$ mm$^{-2}$ s$^{-1}$.

The target may be made of tungsten or tungsten alloy. In some examples, the outer surface of the target may be formed of tungsten or a tungsten alloy and the core of the target is formed of copper. This can reduce weight and increase heat conduction. The outer surface of the target may have a thickness of at least 5 mm and/or at most 10 mm.

The system may further have either:
(A) a collimator having one or more micro-beam forming apertures which collimate the produced x-rays into one or more respective micro-beams, the, or each, micro-beam forming aperture having a given shape on a cross-section therethrough perpendicular to the formed micro-beam, wherein the focal spot has substantially the same shape as a projection of the cross-sectional shape of the aperture(s) onto the target surface at the focal spot; or
(B) no collimator to collimate the produced x-rays, or a collimator other than collimator (A).

BRIEF DESCRIPTION OF THE DRAWINGS

Embodiments of the invention will now be described by way of example with reference to the accompanying drawings in which.

DETAILED DESCRIPTION AND FURTHER OPTIONAL FEATURES

We describe below in a first subsection the production of x-ray micro-beam radiation and then in a second subsection the production of high brilliance x-rays.

Production of X-Ray Micro-Beam Radiation.

Figure 1B:
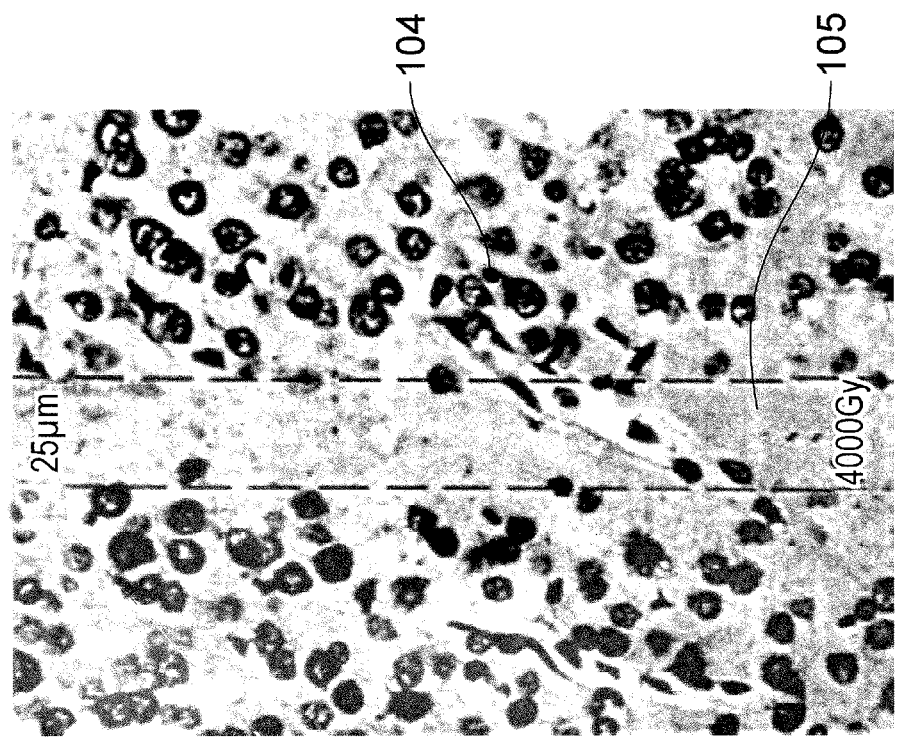
FIGS. 1A and 1B (from Zeman et al. Radiation Res. 15 (1961), 496) show, respectively, the effects of ionising radiation on biological tissue.
Figure 1A:
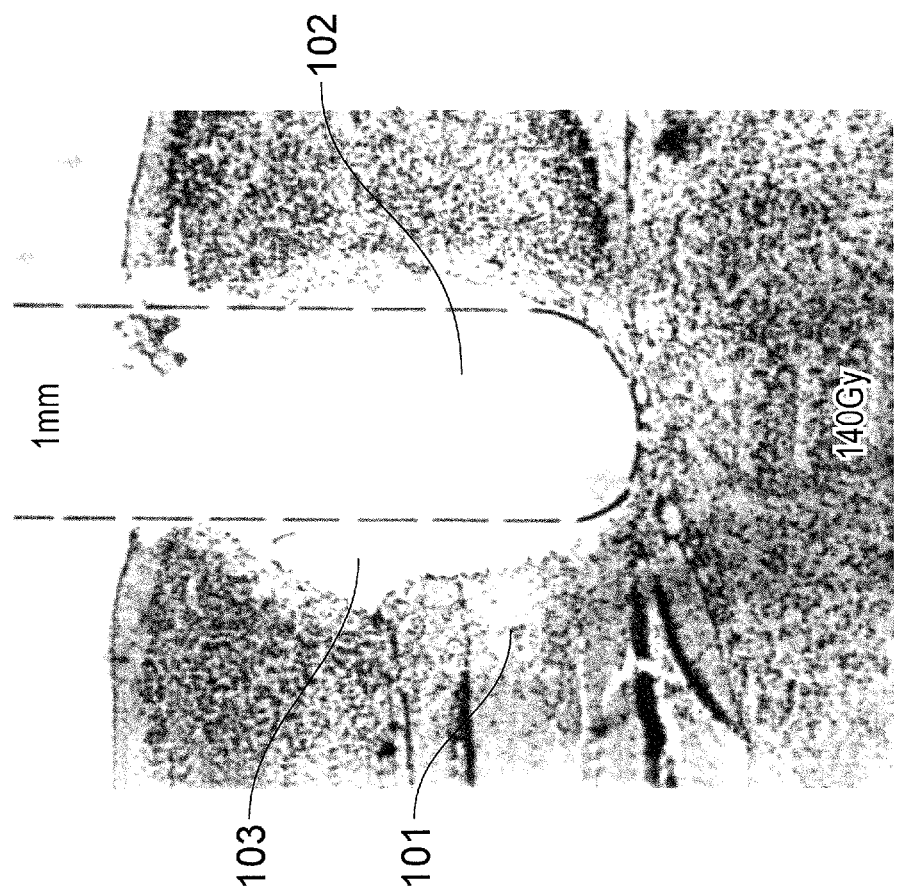

With reference to FIGS. 1A and 1B, there are shown two biological samples (from Zeman et al. Radiation Res. 15 (1961), 496) which have been exposed to ionising radiation. The sample tissue 101 in FIG. 1A has been exposed to radiation with a dose of 140 Gy, with a beam width of 1 mm. As can be seen, a region 102 of the tissue has been destroyed and a 1 mm wide void is left within the tissue. However a substantial amount of surrounding tissue 103 has also been injured, which was not within the area directly exposed to ionising radiation. In contrast, a biological sample 104 as shown in FIG. 1B was exposed to ionising radiation with a dose of 4000 Gy but with a beam width of 25 μm. The biological material within area 105, shows a reduction of cell nuclei. However the tissue structure stays intact. This demonstrates that radiation of a small beam width (e.g. less than 1000 μm) results in a substantial reduction in collateral damage to surrounding tissue. Further, a much higher radiation dose, 4000 Gy as compared with 140 Gy, is required to destroy the targeted tissue. This is known as the dose volume effect i.e. as the volume of irradiated tissue decreases the radiation dose required to cause damage to that tissue increases.

Figure 2A:
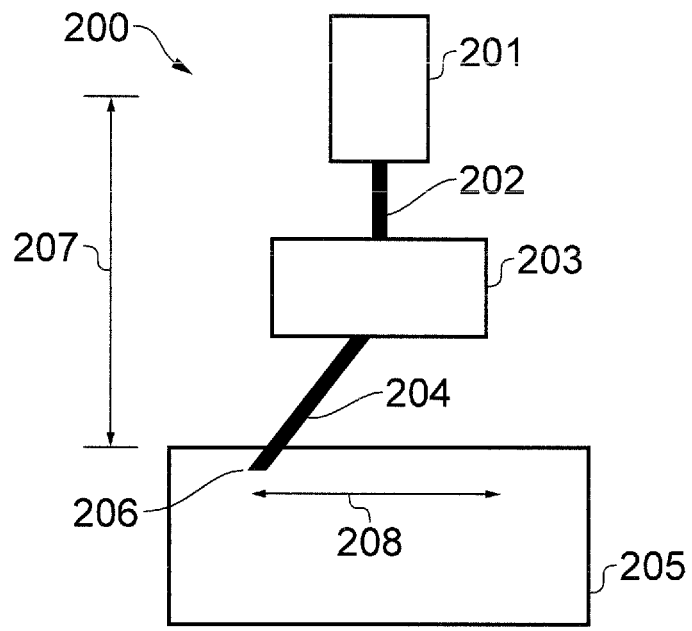
FIG. 2A is a front-on schematic view of an x-ray microbeam radiation production system and FIG. 2B is a side-on schematic view.
Figure 2B:
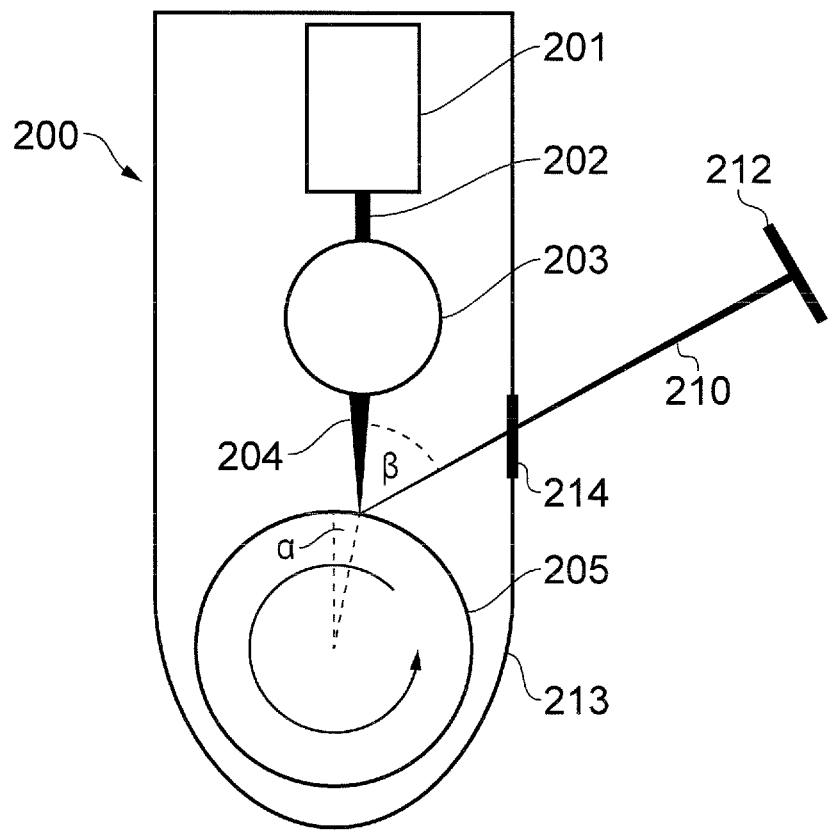

Moving to FIGS. 2A and 2B, a system 200 for producing x-ray micro-beam radiation is shown. More particularly, FIG. 2A shows a front-on view of parts of the system in which the micro-beam radiation is emitted in a plane coming out of the page at an angle β, and FIG. 2B shows a side-on view of the system.

Considering first FIG. 2A, an electron source 201, which might for example be a thermionic electron gun, provides a beam of accelerated electrons 202 which enter an electron focusing component 203. The electron focusing component could, in some examples, be a set of magnets suitable for bending and shaping the beam of electrons through application of a magnetic force. The result of the focusing is a focused electron beam 204, which impinges at a focal spot 206 on a surface of a cylindrical target 205. The target can be, for example, a cylinder with a tungsten or tungsten alloy outer layer and a copper core. The copper promotes heat transfer from the target surface, which is heated by the impinging electrons. There is a distance 207 between the target and the source of electrons, which in this example, is about 500 mm. The focal spot can be generally rectangular with its long axis parallel to the axis of the cylindrical target, and may move along a direction 208 parallel to the cylindrical axis. As the focused electron beam impinges on the target, it causes x-rays to be emitted therefrom in a manner well understood for x-ray tube devices. The electrons may be accelerated by an accelerator, e.g. contained in the electron source, so as to increase the energy of the electrons as they impinge on the target. The accelerator may use a voltage of around 600 kV to accelerate the electrons. Additionally or alternatively, the target may be an anode target to (further) accelerate the electrons.

Turning then to FIG. 2B, as indicated by the arrow, the target can rotate around its cylindrical axis. Also shown in FIG. 2B are: a vacuum housing 213 for the source 201, electron focusing component 203 and target 205; an exit window 214 from the housing; and a multi-slit collimator 212, which forms micro-beams by collimating an angular sector 210 of the x-rays emitted from the target and passing through the exit window. In this example the collimator is around 500 mm from the surface of the target, although this can be adjusted. The x-rays emitted from the target have generally diverging beam paths, although increasing the distance of the collimator from the focal spot reduces the divergence in the formed micro-beams. An angle β exists between a normal to the target surface at the focal spot of the impinging electrons and the collimated part of the emitted x-rays. Similarly, an angle α exists between the incident focused electrons 204 and a normal to the target surface at the focal spot. α can have a value of around 10° and β can have a value of around 60°.

Rotating the cylindrical target 205 moves the focal spot 206 over the surface of the target, and thus helps to prevent the target locally melting at the focal spot. Similarly, moving the focal spot along the direction 208 parallel to the cylindrical axis of the target helps to spread the heat load over a larger area and prevent target melting. In general it is beneficial to adopt both types of movement. The axial movement can, for example, conveniently be achieved by magnetic electron beam deflection in component 203 producing a reciprocating motion of the focal spot over the target cylinder surface. Then, in order to keep the emitted x-rays fixed in space, the whole system, except for the collimator 212, is translated synchronously with an equal and opposite reciprocating motion such that the focal spot 206 remains stationary. An alternative of reciprocating just the target would be possible, but producing a superposition of target rotation and translation within the vacuum of the housing might actually be more challenging than translating the whole housing.

When the electron source 201 is based on thermionic emission, its output can be described by the Richardson Equation:

$$j = A_0 T^2 e^{-\frac{W}{kT}}$$

Where $A_0$ is a constant with value 60 Acm$^{-2}$K$^{-2}$; W is the work function of the metal used in the electron gun (in this case 4.5 eV), k is the Boltzmann constant, and T is the temperature of the metal. For T=2700 K, j=1.75 A/cm$^2$ and for T=3000 K (the likely limit of a cathode), j=14.9 A/cm$^2$.

It should be noted that Schottky emission is not taken into account in the above. Therefore j may have a slightly higher value in actuality than discussed above. Also, space charge will not be an important consideration. As the electrons may be accelerated across a voltage of 600 kV, the system is being operated in its saturation region (i.e. where an increase in acceleration voltage does not result in any substantial increase in electron current, see the space charge law). Hence a 1.0 cm$^2$ filament surface would be sufficient to produce an electron beam of more than 1 A at a surface temperature of 2700 K. The electron beam 202 will have an intensity Φ, where $$\Phi = \frac{I}{8\pi^2 \epsilon_x \epsilon_y}.$$

When the electron source 201 is a thermionic electron gun, the normalised emittance of the electron beam 202 at 3000K can be described as follows:

$$\epsilon_N = \sigma_x \sqrt{\left(\frac{k_b T}{m_e c^2}\right)} = 7.11 \cdot 10^{-4} \sigma_x$$

Where $m_e$ is the mass of an electron (9.11×10$^{-31}$ kg), c is the speed of light in vacuum, and $\sigma_x$ is the root-mean-square beam size.

Therefore, in the case of a 20 mm diameter source, the emittance can be calculated as $\epsilon_N \approx 7.1$ mm·mrad. This value is quite conservative, and it is likely that the emittance can be decreased.

It is also helpful to consider the minimum spot size that the beam can be focused onto. The geometric emittance ∈ can be calculated as follows:

$$\epsilon = \frac{\epsilon_N}{\gamma \beta}; \gamma\beta \approx 1.133; \therefore \epsilon \approx 6.27 \text{ mm·mrad}$$

For a 100 μm width focal spot, the divergence in this example would be 0.0627 rad=3.59° at the focal spot. Therefore the beam may have to hit the target surface such that the long axis of the rectangular focal spot is perpendicular to the incoming electron beam.

Figure 3:
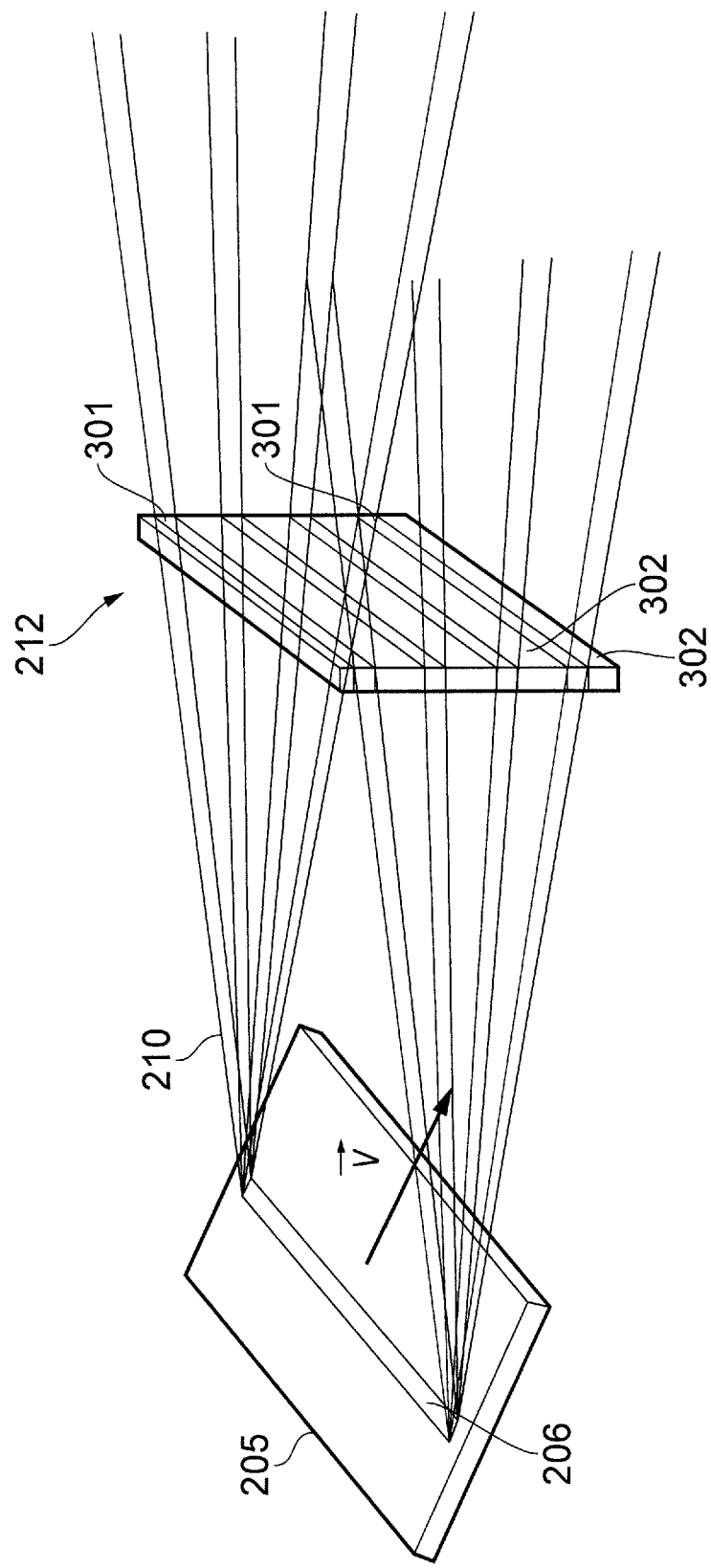
FIG. 3 is a schematic view of a collimator of the system and part of a target of the system.

Moving now to the collimator 212, this is shown in more detail in FIG. 3, along with an extract of the target 205 surface. The collimator comprises a number of slits 301 and blanks 302. The slits are generally rectangular in cross-section to have substantially the same shape as the rectangular focal spot 206 when they are projected onto the target surface. The slits may thus have a cross-sectional width of 50 μm in this example to produce a projected width of about 100 μm, i.e. the same width as the focal spot. Shaping the collimator openings such that their projections are congruent with the focal spot helps to avoid partial shadowing of the source along the micro-beams downstream of the collimator. The photon fluence in the micro-beams can hence be equal to an open field geometry.

Figure 4:
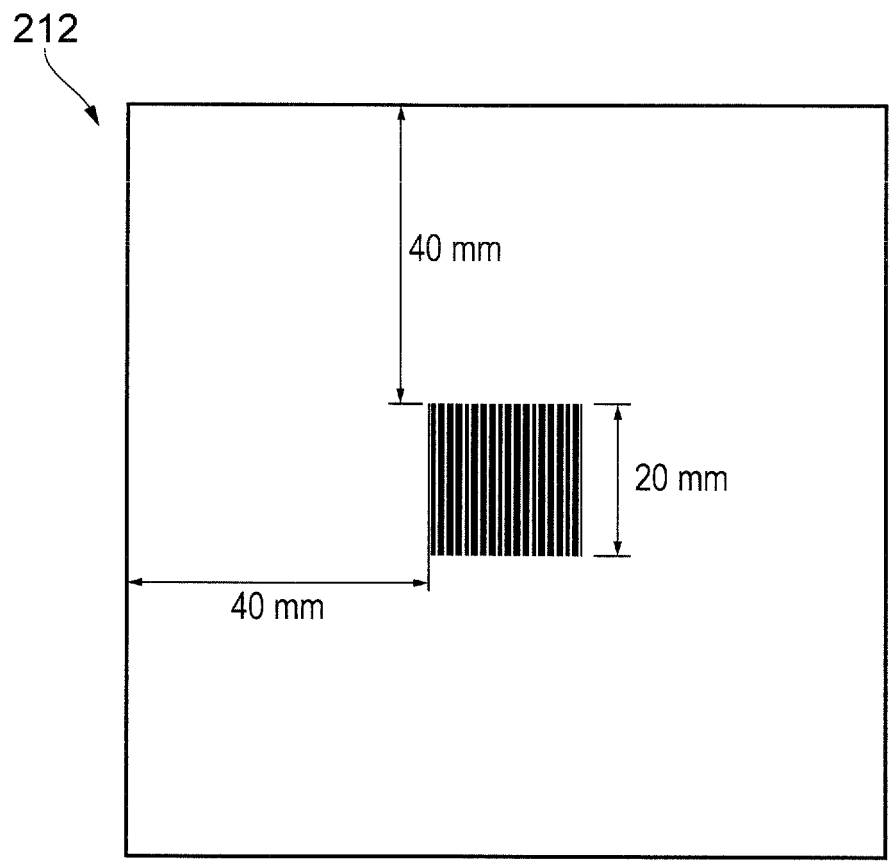
FIG. 4 is a schematic plan view of the collimator.
Figure 5:
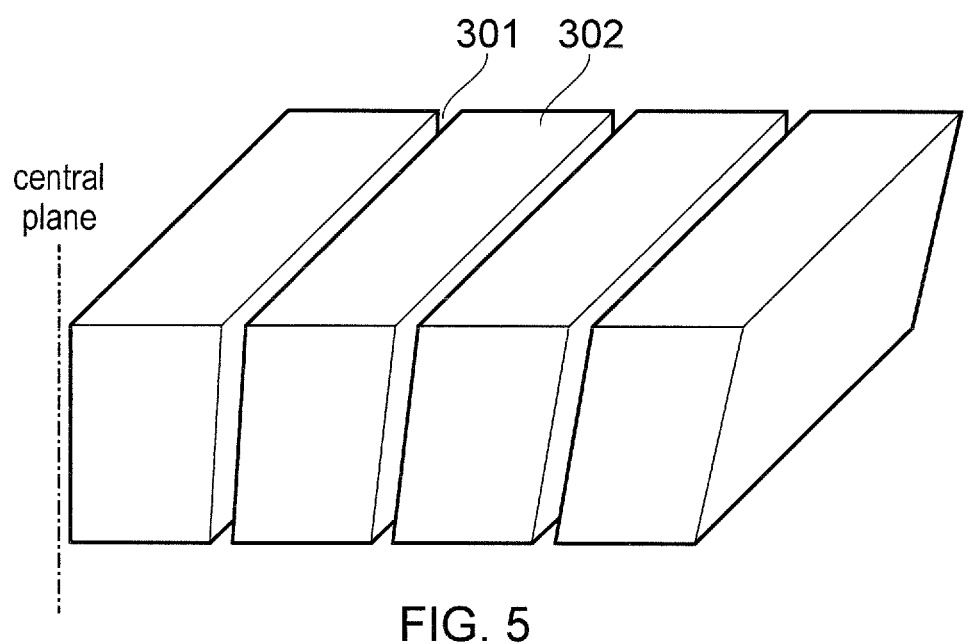
FIG. 5 is a partial cross-section of the collimator.

Further details of the collimator are shown in FIGS. 4 and 5. Generally the collimator 212 is formed from a large plate of a suitable material to absorb incident x-rays e.g. lead. As shown in the plan view of FIG. 4, an array of slits 301 is provided in the plate. The collimator is typically configured for a given focal spot to collimator distance, which in this example is 7 cm. The array is around 20×20 mm$^2$, and comprises forty-nine 50 μm wide and 20 mm long slits. A schematic partial cross-section of the collimator plate is shown in FIG. 5. Especially for short focal spot to collimator distances and for thick collimators the slits can have an inclination towards the perpendicular of the collimator surface in order to account for the divergence of the radiation field. Wire cutting can be used to form the collimator slits. In particular, small holes can be drilled at opposing ends of the array, and the cutting wires inserted therethrough.

Figure 6:
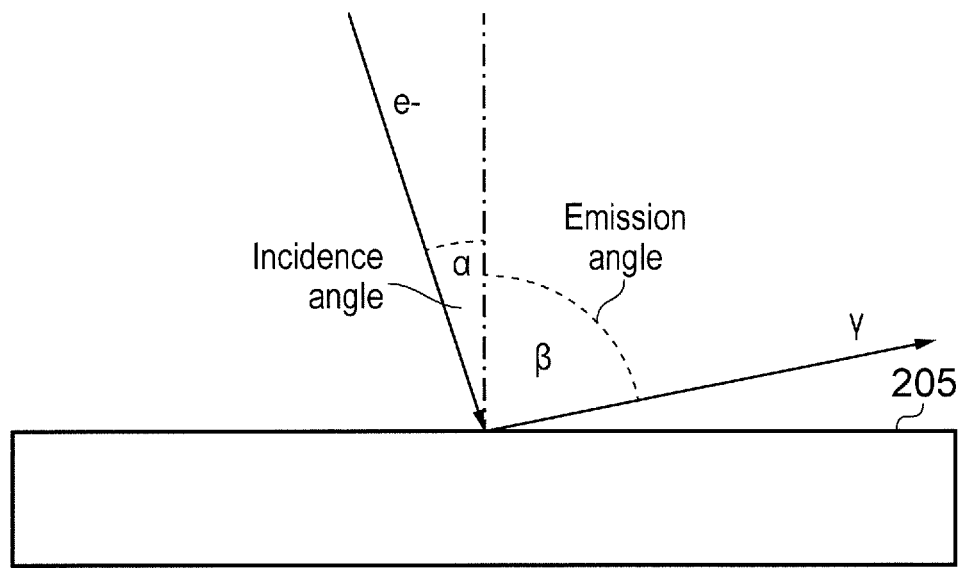
FIG. 6 is a schematic view of the surface of the target.
Figure 7:
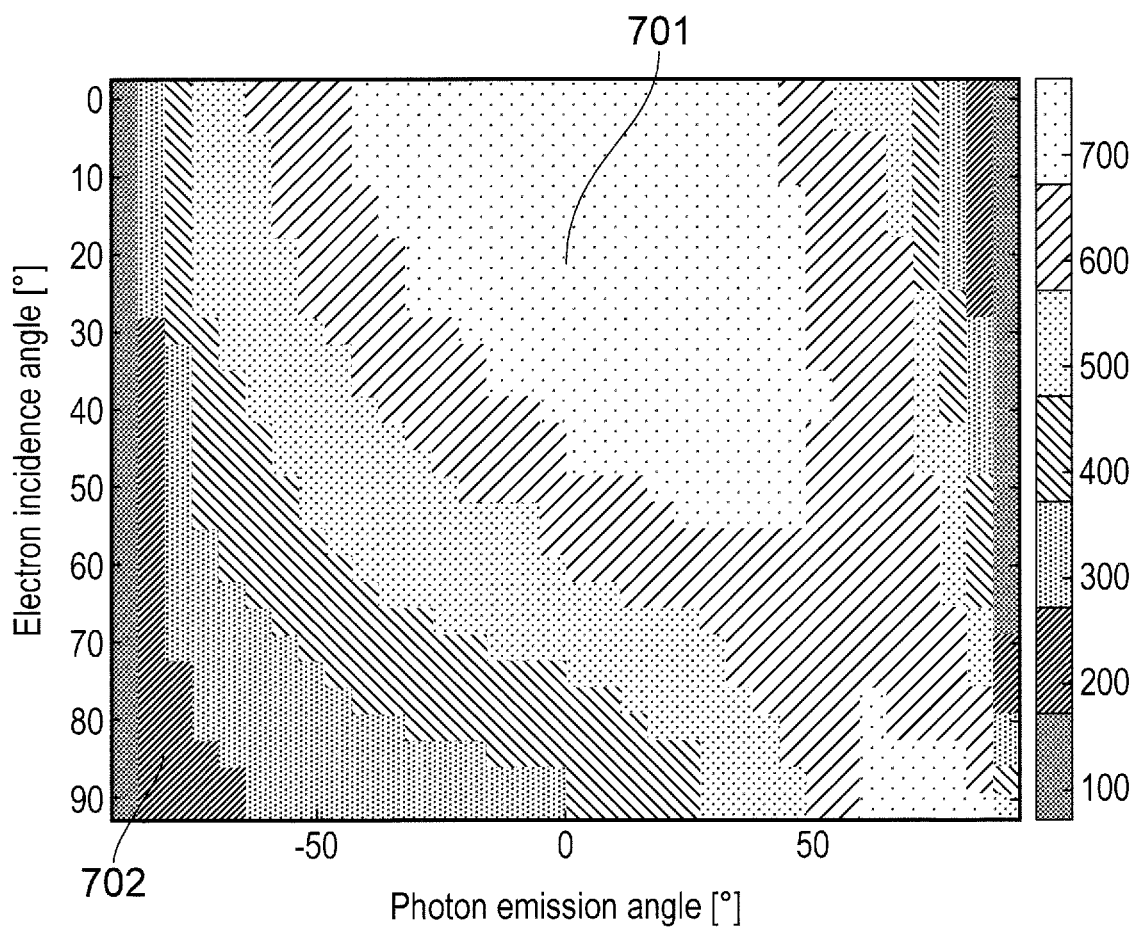
FIG. 7 is a plot of photon yield as a function of electron incidence angle and photon emission angle.

As was shown in FIG. 2B, and is further illustrated in FIG. 6, an angle α exists between a normal to the target 205 surface at the focal spot and the incident electron beam e$^-$. This angle α is referred to as the incident angle. Similarly, there is an angle β between the normal to the target at the focal spot and an emitted x-ray beam γ. This angle β is referred to as the emission angle. FIG. 7 shows a plot of photon yield (in parts per million) as a function of both incidence and emission angles. The region 701 shows the largest photon yield of around 700-800 ppm, and region 702 shows the smallest yield of between 50-200 ppm. This plot demonstrates that for an incidence angle of 10° or less a good photon yield can be achieved across a relatively broad range of emission angles (e.g. −60° to +60°). Generally it can be stated that the plot shows that photon intensity is high for small incidence angles and that perpendicular to the plane shown in FIG. 6 the intensity follows Lamberts law:

$I(\theta) = I_0 \cos(\theta)$

Where θ is the angle relative to the plane in FIG. 6 and $I_0$ is the intensity for θ=0.

Figure 8:
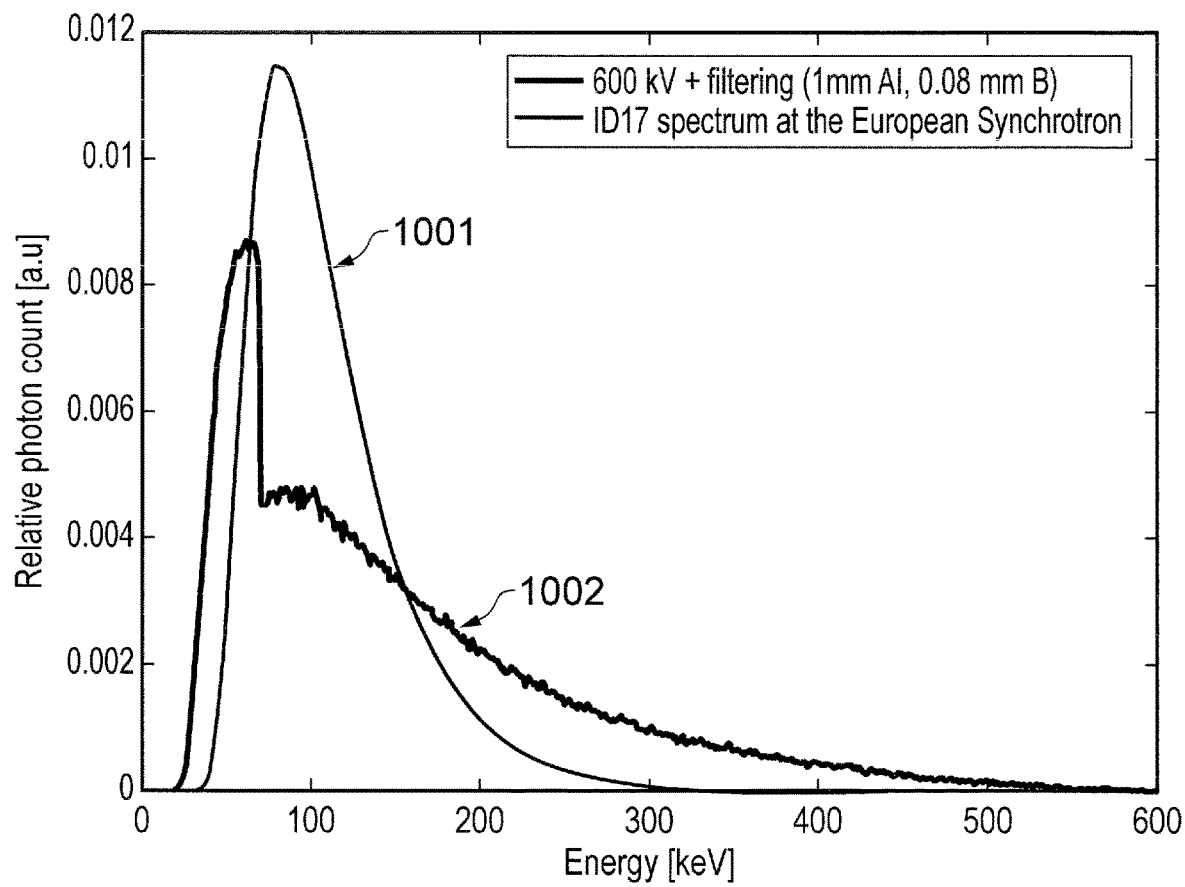
FIG. 8 compares the photon count spectrum of a 600 kV x-ray tube and the synchrotron beam of ID17 at the European Synchrotron.

FIG. 8 compares the photon count spectrum of a 600 kV x-ray tube (tungsten target, 1 mm Al filtering) and the synchrotron beam of ID17 at the European Synchrotron presently used for most preclinical micro-beam irradiations. Line 1001 is the synchrotron spectrum (see e.g. Crosbie et al., J. Synchrotron Rad. 22, 1035-1041 (2015)). The beam is peaked at around 80 keV and has a mean energy of 110 keV. There is no significant contribution of photons with energy below 40 and above 300 keV. Whereas, line 1002 shows the spectrum of a 600 kV x-ray tube of a type which may be used in the present invention. The spectrum is significantly wider than the synchrotron spectrum and a significant photon contribution is expected between 25 and 500 keV. The mean energy is around 149.2 keV, 18.3% of the primary beam being absorbed by the Al filtering.

Table 1 below shows in column 2 the measured dosage rate of a conventional 160 kV x-ray tube with a power of 1.8 kW, a tungsten target and a 1 mm thick Al filter for distances of between 100 and 500 mm. As shown in column 3, a dosage rate per kW can thus be estimated for the conventional tube. From these measurements the expected dose rate per kW for the micro-beam radiation production system described above can be calculated by Monte Carlo simulations. Due to an increased efficiency in the electron-photon conversion in the target and higher photon energies the dose rate is expected to be 16.2 times higher. The expected dose rates per kW for the system can be found in column 4. As discussed later, the maximum power of the system is limited by the surface velocity of the rotating anode. Assuming a surface velocity equivalent to that of a standard spinning disk x-ray tube anode of 178 m/s the power limit would be 712 kW. This leads to maximum expected dose rates of between 3660 Gy/s and 147 Gy/s at distances between 100 and 500 mm from the focal spot, as indicated in column 5.

Table 2 below shows the change in centre-to-centre distance, beam width, and beam penumbra with varying focal spot to collimator distance:

TABLE 2

| Distance [mm] | Centre-to-centre [µm] | Beam width [µm] | Beam penumbra [µm] |
|---|---|---|---|
| 0 | 400 | 50 | 0 |
| 50 | 440 | 55 | 5 |
| 100 | 480 | 60 | 10 |
| 150 | 520 | 65 | 15 |
| 200 | 560 | 70 | 20 |
| 250 | 600 | 75 | 25 |
| 300 | 640 | 80 | 30 |
| 350 | 680 | 85 | 35 |

Figure 9:
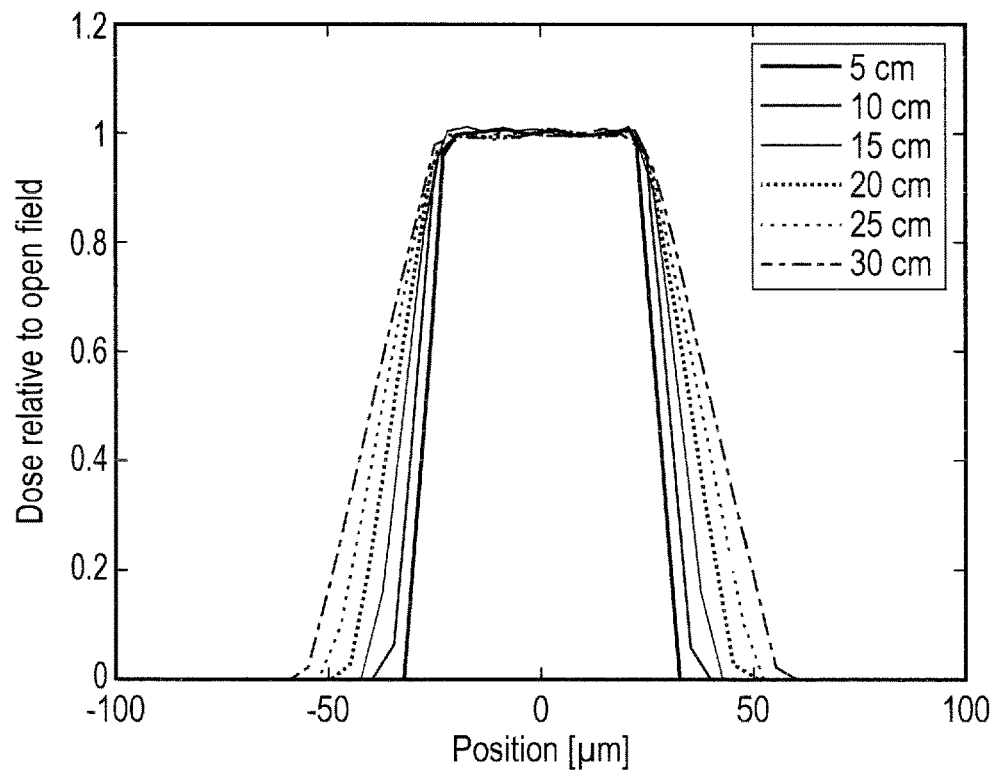
FIG. 9 shows profiles of photon fluence perpendicular to a micro-beam axis for various patient treatment depths at a focal spot to collimator distance of 500 mm.
Figure 10:
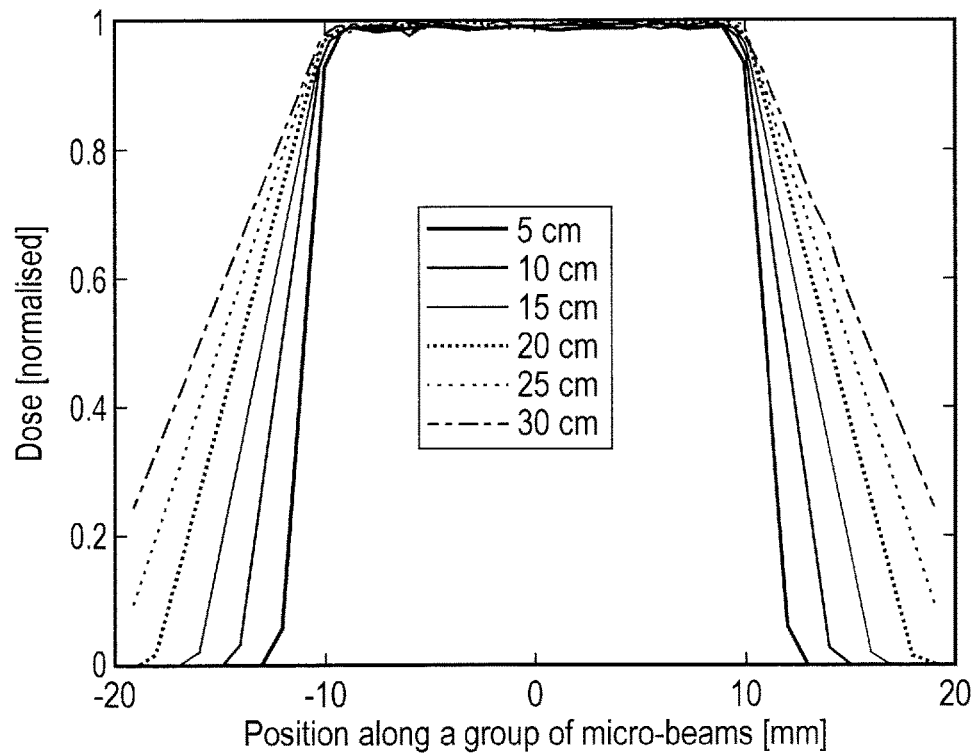
FIG. 10 shows profiles of photon fluence along the micro-beam length for various patient treatment depths at a focal spot to collimator distance of 500 mm.

It should be noted that FIGS. 9 and 10 only take into account primary photon fluence (photon rate per surface unit area) and assume a perfect absorber (i.e. 100% absorption in the collimator material). Scattering was not taken into account.

Figure 11:
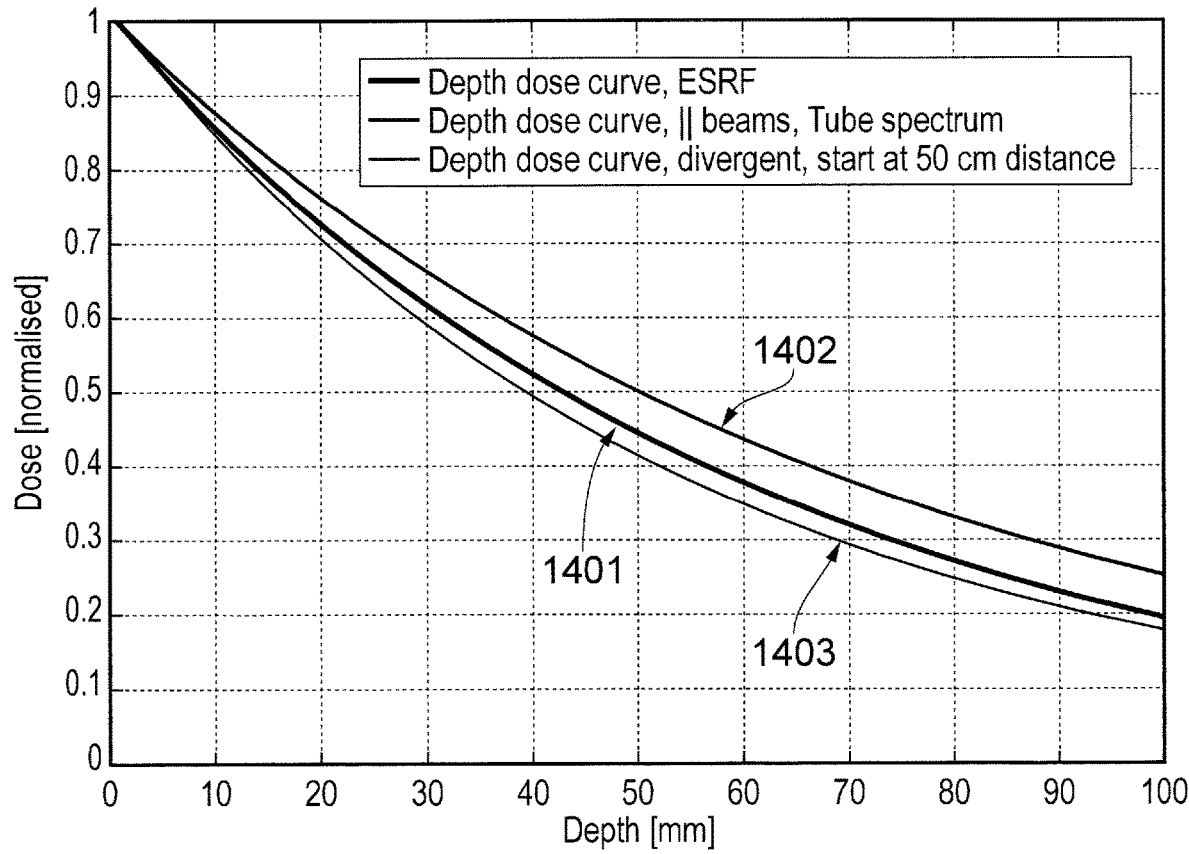
FIG. 11 is a plot of radiation dose against depth for a number of radiation sources.

FIG. 11 is a plot of dose as a function of depth into a specimen for three different radiation sources. In all cases, the specimen was water. The depth dose curve for radiation produced at the European Synchrotron Radiation Facility (ESRF) is denoted by line 1401. The line 1402 shows a depth dose curve for radiation produced with parallel beams and with an x-ray tube spectrum. As can be seen, this source provides a greater dose relative to the ESRF source as a function of depth. However truly parallel beams, such as might be provided by a synchrotron radiation source, cannot

TABLE 1

| Distance [mm] | Dosage rate at 160 kV and 1.8 kW [Gy/s] | Dosage rate at 160 kV and 1 kW [Gy/s] | Dosage rate at 600 kV and 1 kW [Gy/s] | Dosage rate at 600 kV and 712 kW [Gy/s] |
|---|---|---|---|---|
| 100 | 0.5715 | 0.3175 | 5.14 | 3660 |
| 200 | 0.1429 | 0.0794 | 1.29 | 919 |
| 300 | 0.0635 | 0.0353 | 0.572 | 407 |
| 400 | 0.0357 | 0.0198 | 0.321 | 229 |
| 500 | 0.0229 | 0.0127 | 0.206 | 147 |

Moving to FIG. 9, this shows absorber free photon fluence cross-sections perpendicular to a single beam of micro-beam radiation as produced by the system discussed above for a focal spot to collimator distance of 500 mm at different patient treatment depths. The photon fluence is relative to the open field, i.e. it has been normalised relative to non-collimated radiation. As compared to parallel synchrotron radiation, the x-ray source of the system will cause beam penumbras with distance from the collimator. The six lines in the plot, show the effect on the photon fluence profile for a number of depths (distances between collimator and measurement point) relevant in patient treatment. As is common to all of the lines, the relative fluence in the beam is 1, meaning the absence of any partial source shadowing. This shows that the micro-beam radiation produced by the system can provide dose profiles with sufficiently sharp beam penumbras. Even at 30 cm depth the width of the penumbra is just 30 µm and hence much smaller than peak-to-peak distance of around 400 µm.

FIG. 10 shows absorber fluence profiles along the length of the micro-beam. As with FIG. 9, six lines are shown, each corresponding to a different patient treatment depth. The beam divergence also affects the length of the micro-beams. For example, the narrowest radiation dose profile (corresponding to 5 cm treatment depth) has a total dose profile width of around 26 mm.

be produced by an x-ray tube. Line 1403 indicates a depth dose curve for an x-ray tube with diverging beams, starting at a distance of 50 cm from the target surface. All of the dose curves have been normalised relative to their respective maximum values. As is shown by the plots in FIGS. 9, 10, and 11 the beam shapes and depth dose curves are very similar to those produced at the ESRF. The x-ray tube beam penumbras remain acceptably small, although they are slightly wider than those seen at the ESRF.

It is useful at this stage to discuss the concept of the efficiency of an x-ray tube. Generally, this can be defined as $\eta$, where $\eta$=Energy Used/Grays Produced. From Table 1, for a 600 kV x-ray tube at a distance of 500 mm, $\eta$ can be calculated as $\eta$=4.85 kJ/Gy. From this value for $\eta$, it can be seen that to produce a 500 Gy peak entrance dose at 500 mm, which would approximately be required for a micro-beam treatment, 2.425 MJ are required. Most of this energy will be deposited as heat into the target. This is sufficient energy to heat 6.5 kg tungsten up to its melting point. This energy needs to be efficiently dissipated when working at high dose rates.

To investigate the temperature rise of the focal spot on a rotating target, the Oosterkamp (1948) equation can be used, $$\Delta T = \frac{2P}{A}\sqrt{\frac{\Delta t}{\pi k \rho c}},$$

where ΔT is the change in temperature, P is the power of the electron beam, A is the area of the focal spot, and Δt is the dwell time. For tungsten the specific heat capacity c=138 J/(kg·K); thermal conductivity k=170 W/(m·K); and density ρ=19.3 g/cm⁻³. For a target which is rotating, $$\Delta t = \frac{2\delta}{v},$$

where v is the surface velocity of the target and δ is the focal spot width.

Therefore, rearranging the Osterkamp equation, for a maximum ΔT at the surface velocity of the target, v is given by v=αP² where α is a constant. Assuming a tungsten target with a 100 μm wide and 20 mm long focal spot (and a 60° emission angle and therefore a 50 μm slit width)

$$\alpha = 0.0225 \cdot \frac{m/s}{kW^2}.$$

The Osterkamp equation can be derived by solving the heat equation assuming that the heat is supplied at the target surface only (Neumann boundary condition). This assumption is valid as long as the heat diffusion range, while a certain point on the surface is hit by the electron beam, is much larger than the electron penetration depth into the target material.

Figure 12:
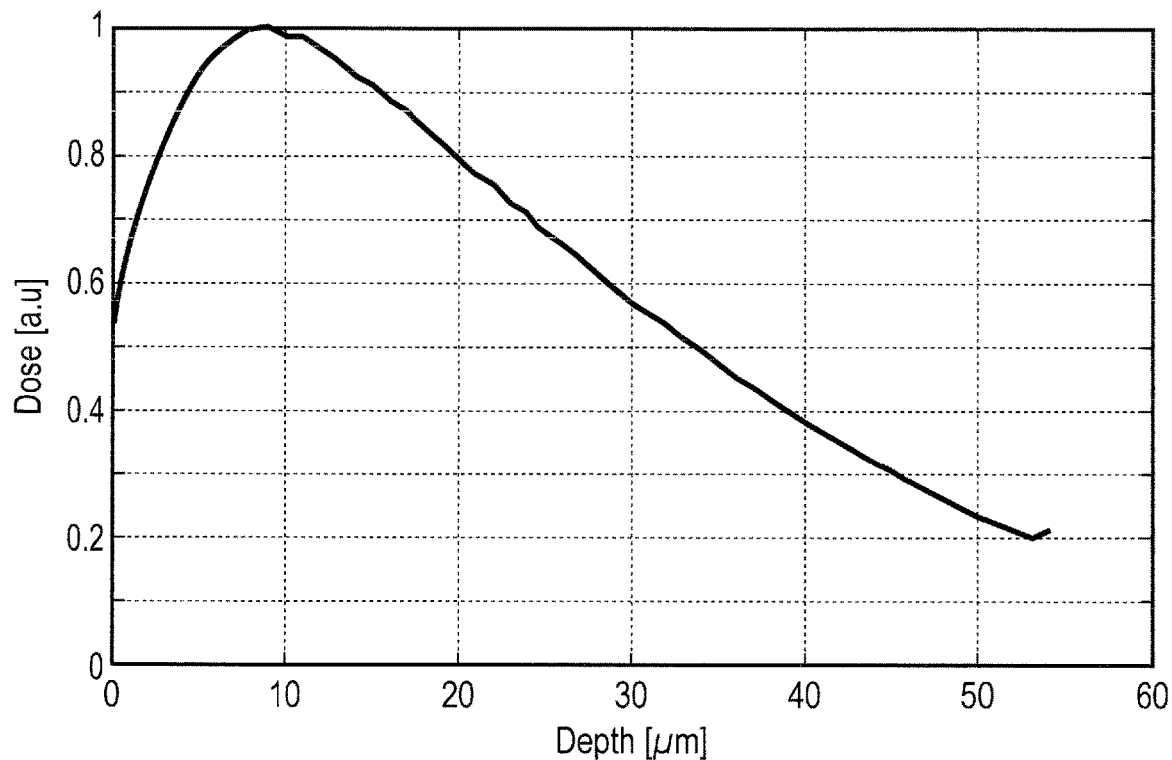
FIG. 12 shows the depth dependent energy deposition of a 600 keV electron beam in tungsten.

If this assumption cannot be made, i.e. at very high surface velocities, the electron absorption volume acts as a source within the target material. The heating is then much faster than the heat conduction, and therefore the relation PδT=ρcVΔT can be used, where V is the electron absorption volume. FIG. 12 shows a depth dose curve of 600 keV electrons impinging on the target. From this a maximum penetration depth of 30 μm is a reasonable and conservative assumption. Using otherwise the same dimensions above:

V≈20 mm×100 μm×30 μm $$v = \frac{2\delta}{\rho V c \Delta T} P = 0.25 \cdot \frac{\frac{m}{s}}{kW} \cdot P$$

From this consideration it follows that the target heating will always be limited by the most rapid of the two above processes.

Figure 13:
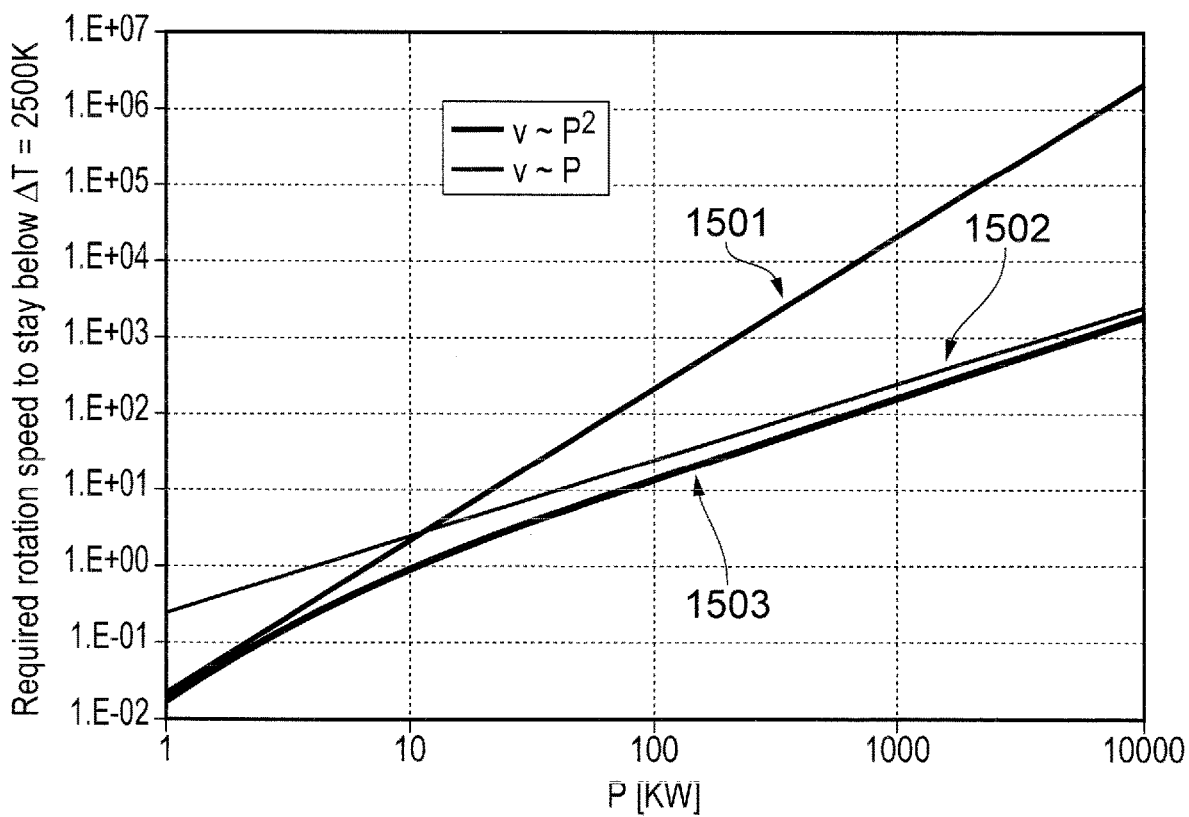
FIG. 13 is a log-log plot of rotational speed against power of the electron beam.

This can be seen in FIG. 13, which is a log-log graph of the rotational speed required for the target to stay below 2500 K as a function of the power of the electron beam. Line 1501 presents the Oosterkamp curve, where target heating is limited by heat conduction, while line 1502 corresponds to the high velocity domain, where target heating is limited by the heat capacity of the target material. Line 1501 is proportional to P² and therefore steeper than line 1501, which is just proportional to P. Line 1503 shows the actually required surface speed depending on the power of the electron beam. A more detailed discussion of the production of high brilliance x-rays using target heating limited by the heat capacity is provided in the next subsection.

Conventionally, x-ray tubes using a spinning disk target can spin at rates of up to 17,000 rpm. Assuming a 100 mm radius disc, this would result in a surface velocity of the target of around 178 m/s which would result in a power limit of the x-ray tube of around 712 kW. This is clearly in the linear part of the required surface-speed to power relation. To operate at this power level in a 600 kV x-ray tube would require an electron current of around 1.19 Amps. It may be possible to rotate the target such that it has a much higher surface velocity of 800 m/s, at such speeds it would be possible to have a 3 MW output. In the following, a conservative maximum power of 712 kW for the system will be assumed.

It is also important to take into account the cooling of the target whilst it is not being exposed to the electron beam. After one rotation, the surface of the target will have cooled down to approximately:

$$T = 0.5 T_R \sqrt{\frac{\delta}{\pi R}} = 15.77 \ K;$$

where $T_R$ is the initial temperature (i.e. 2,500K), δ is assumed to be 50 μm, and the radius of the target R is assumed to be 0.1 m. After each revolution of the target, the surface temperature will increase.

Figure 14:
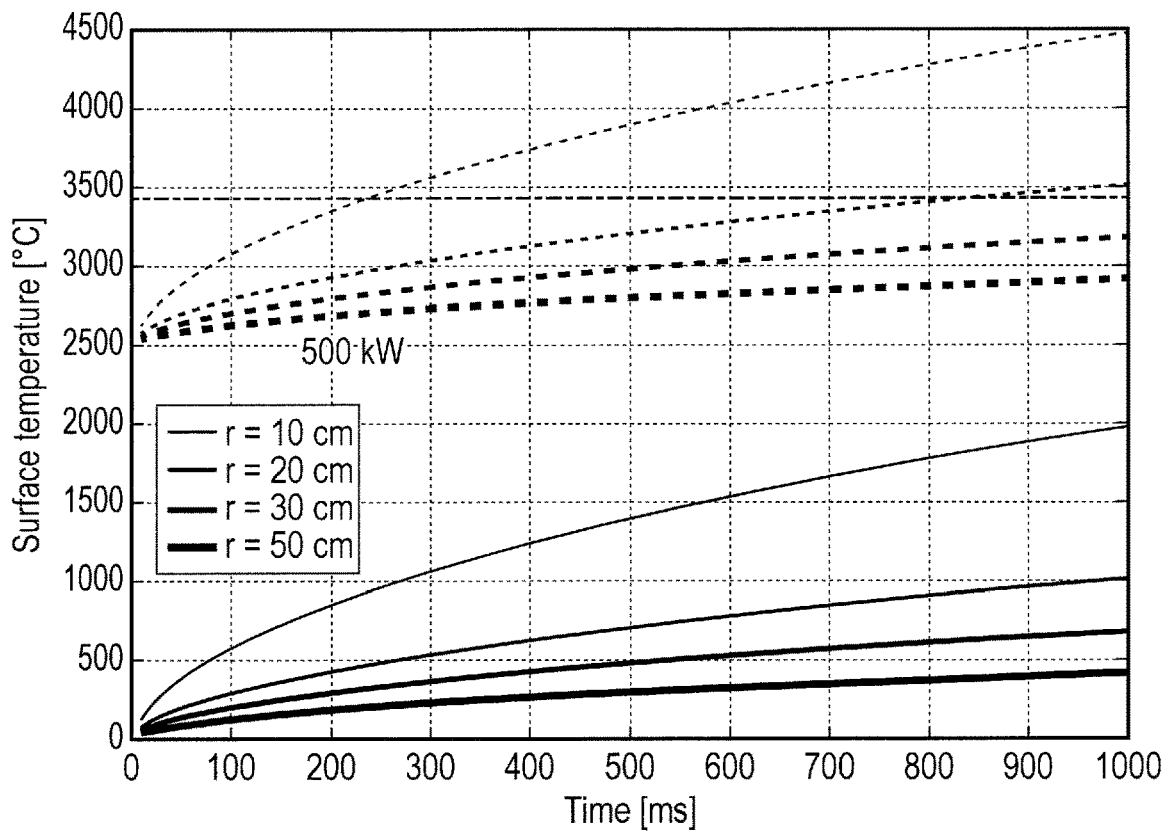
FIG. 14 shows plots of average and peak surface temperatures against time for a 500 kW x-ray tube, various target radii at 178 m/s surface velocity of the rotating target, a focal spot length of 2 cm and no reciprocating motion of the target.
Figure 15:
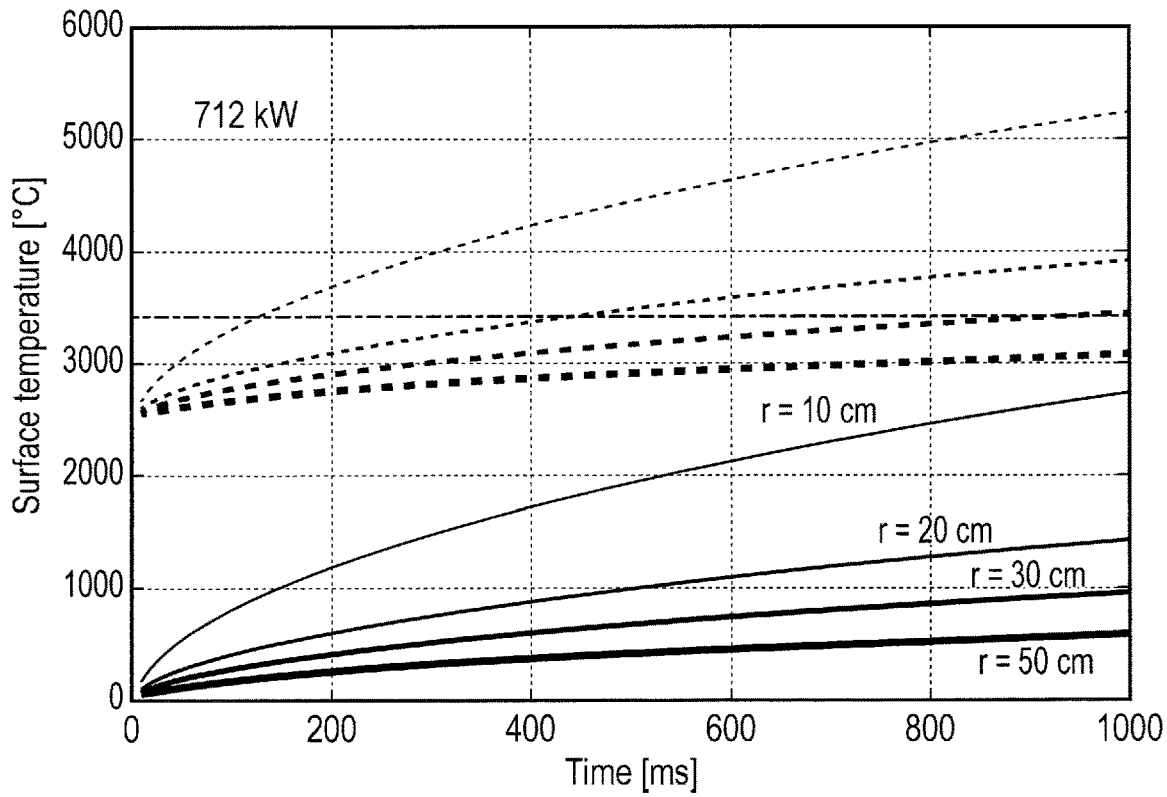
FIG. 15 shows plots of average and peak surface temperatures against time for a 712 kW x-ray tube, various target radii at 178 m/s surface velocity of the rotating target, a focal spot length of 2 cm and no reciprocating motion of the target.

For longer time periods the heat equation needs to be solved. Results of solving the heat equation for this situation are shown in FIGS. 14 and 15 for a 500 kW and 712 kW x-ray tube respectively. In these plots the dotted lines indicate the temperature of the surface of the target just after it was hit by the focal spot and the solid lines indicate the temperature of the surface of the target just before it is hit again by the focal spot. The black dotted line represents the melting temperature of tungsten (3,422° C.). There are four sets of lines on each graph, representing targets of varying radius. The uppermost solid/dotted line represents a target with a radius of 10 cm, and the lowermost solid/dotted line represents a target with a radius of 50 cm. From these plots it can be seen that in order to maintain a high output over time scales of around 1 s, the target radius must be of an appropriate size, or the heat must otherwise be distributed over a larger surface area, e.g. by a reciprocating motion of the focal spot along the target cylinder axis.

From the above analysis, two general statements can be made:

The maximum dose rate depends solely on the surface speed of the target; and

The maximum dose that can be delivered, at a fixed dose rate and focal spot length, depends only on the area the heat is spread on the target surface.

Table 3 shows the variation of exposure time (and therefore maximum dose) for targets of two different radii. These values are given for a 500 mm distance between the collimator and focal spot on the target, the Gray values are peak entrance doses for a dosimetry phantom positioned directly in front of the collimator.

TABLE 3

| Radius [cm] | Exposure Time at 250 kW [s] | Dose at 250 kW [Gy] | Exposure Time at 500 kW [s] | Dose at 500 kW [Gy] | Exposure Time at 715 kW [s] | Dose at 712 kW [Gy] |
|---|---|---|---|---|---|---|
| 30 | 7.00 | 360.5 | 1.80 | 185.4 | 0.91 | 133.8 |
| 50 | 19.39 | 998.6 | 4.89 | 503.7 | 2.45 | 360.2 |

The maximum achievable tube power (given the assumptions made) is 712 kW. With a target with a diameter of 1 m the maximum dose which can be delivered is around 360.2 Gray. Whilst 250 kW and 500 kW power levels may achieve a greater total dosage, the dose rate (i.e. Gy/s) is significantly lower. High dose rates, however, are essential in clinical micro-beam treatments, in order to avoid blurring of the dose distribution e.g. by cardiovascular motion.

Preferably the target has a smaller diameter than 1 m, as there are significant technical, energy consumption and safety issues associated with spinning large objects at high frequencies. One method of reducing the diameter of the target is to translate the focal spot of the electron beam along the surface of the target in use, as discussed above in relation to FIGS. 2A and 2B.

Figure 16:
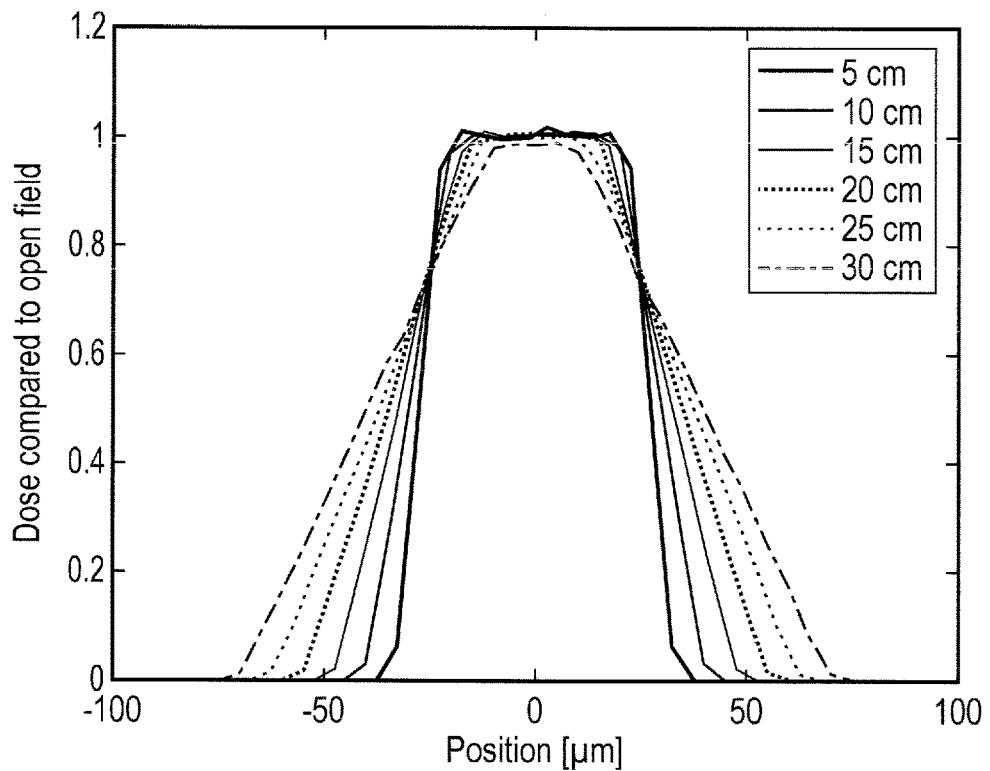
FIG. 16 shows profiles of photon fluence rate perpendicular to a micro-beam axis for various patient treatment depths at a focal spot to collimator distance of 500 mm, and a larger focal spot size than that of FIG. 9.

A further option to increase the dose and dose rate is to increase the focal spot length and width, whilst keeping the collimator dimensions constant. Therefore the amount of x-ray radiation generated may be doubled, whilst still allowing the collimator to produce micro-beam radiation. Increasing the focal spot length and width by a factor of 2 would give a factor of 4 increase in dose rate and a factor of 2 increase in dose. The focal spot would still be substantially the same shape as the slits in the collimator, but would be larger in size. The beam shape would be slightly deteriorated. FIG. 16 shows equivalent profiles to those of FIG. 9, but for the larger focal spot size. Whilst the beam-penumbra is wider than before (FIG. 9) it might still be acceptable for radiological purposes. It may also be possible to increase the width and length of the focal spot by a factor of 3.

One more option to increase the dose and dose rate is to move the collimator closer to the surface of the target. In principle 200 mm can be used, and would give a factor of 6.25 increase in dose and dose rate. However there would be a higher beam divergence, and therefore the depth dose curve would not be as favourable. Also beam width and beam-to-beam spacing would more rapidly increase with distance from the collimator.

Table 4 provides a comparison of various key parameters between micro-beam radiation as produced by a synchrotron and micro-beam radiation as produced by an x-ray tube according to the present invention:

cant increase in electron beam current density without raising the focal spot temperature above the melting point of tungsten.

In conventional rotating anode x-ray tubes, heat conduction limits the temperature increase in the focal spot. An electron beam power $P_{cond}$ is absorbed at a focal spot surface area $A=\delta h$, and almost completely converted into heat. The heat is dissipated by heat conduction and the focal spot temperature increase $\Delta T$ during an exposure time $\Delta t$ is proportional to the electron beam intensity $P_{cond}/A$ at the focal spot (Oosterkamp W. *Calculation of the Temperature Development in a Contact Heated in the Contact Surface, and Application to the Problem of the Temperature in a Sliding Contact*. Journal of Applied Physics. 1948; 19(12): 1180-1; and Oppelt A, Kutschera W, Behner H, Bernhardt J, Neumeier E, Ponnath P, et al. *Imaging systems for medical diagnostics*. 2nd edition ed. Erlangen: Publicis MCD; 2005):

$$\Delta T = \frac{2P_{cond}}{A}\sqrt{\frac{\Delta t}{\pi k \rho c}}$$

where k, ρ and c denote heat conductivity, density and heat capacity of the target material. For a rotating anode $\Delta t$ will be $\delta/v$ and, assuming a fixed maximum temperature rise $\Delta T_{max}$ the target can withstand, the maximum electron beam power is:

$$P_{cond} = \gamma_1 h\sqrt{v\delta}, \gamma_1 = \sqrt{\frac{1}{4}\Delta T_{max}^2 \pi k \rho c}$$

However, as the previous equation for $\Delta T$ is a solution of the heat equation with Neumann boundary conditions, it only assumes a surface heating at an electron beam intensity

TABLE 4

|  | European Synchrotron (ESRF) | X-ray tube |
|---|---|---|
| Dose rate | 15,000 Gy/s; Effectively*: 375 Gy/s | Average: 147 Gy/s Upper limit: ≈1200 Gy/s |
| Beam divergence | Parallel Beams; Steep beam penumbras | Divergent beam; For example, in a 100 mm deep phantom: ctc of 400-480 μm; beam penumbra of up to 10 μm |
| Depth dose curves | Depth independent | Depth dependent, but beginning at about 500 mm similar to the synchrotron |
| Energy consumption | ≈2.5 MW continuously | 1 MW-4 MW for a few seconds |
| Beam switching mechanism | Mechanical, therefore difficult and slow | Electric (no current = no beam); fast |
| Movability | Immovable | Can be moved around patient |

*The field height at the European Synchrotron is about 500 μm. Therefore patients need to be scanned vertically through the beam. The effective dose rate is hence lower than the nominal 15,000 Gy/s Production of High Brilliance X-Rays The system 200 shown schematically in FIGS. 2A and 2B and discussed in the above subsection, generates, accelerates and electromagnetically shapes an electron beam 202 that hits the fast rotating, typically tungsten, cylindrical target 205 in a thin focus line, i.e. a focal spot, with a very large aspect ratio h/δ, where h and δ are the length and width of the focal spot 206, respectively. The surface velocity of the focal spot across the target surface in the width direction is v. Changes in the physics of the target heating at high values of v and small spot widths advantageously permit a signifiof $P_{cond}/A$. The range of electrons in the target material is completely ignored, which is a valid assumption as long as the heat diffusion length $l_d$ during electron beam exposure time $\Delta t$, $$l_d = 2\sqrt{\frac{k\Delta t}{\rho c}},$$

is much larger than the electron range $l_e$, $l_d \gg l_e$.

This changes for large surface velocities v, narrow spot widths δ and large electron penetration depths at high acceleration voltages, though. If the electron range $l_e$ is significantly larger than the heat diffusion length $l_d$, $l_e \gg l_d$, the heating of the target material is limited by the heat capacity only. A volume element δV receiving the heating power δP by electron absorption, heats according to $$\delta P \Delta t = \rho \delta V c \Delta T.$$

For a fixed maximum temperature increase $\Delta T_{max}$ this leads, in contrast to the above equation for $P_{cond}$, to a maximum electron beam power of $$P_{cap} = \gamma_2 v l d, \gamma_2 = \rho c \Delta T.$$

Here the electron penetration depth is denoted by d and depends on the electron beam energy and the anode material. An accurate definition of d is provided in the Appendix. Importantly, $P_{cap}$ does not depend on the focal spot width δ. Hence a reduction in focal spot width does not impact on the maximum possible electron beam power anymore. The intensity $P_{cap}/A$ of the electron beam can be increased ad libitum by reducing the focal spot width and is only limited by lateral scattering of electrons in the target which is approximately given by $\delta_{min} \approx d/3$ (see also Appendix, "Estimation of $\delta_{min}$").

The transition from the conventional heat conduction limit ($l_d \gg l_e$) to the heat capacity limit ($l_e \gg l_d$) occurs when $P_{cap} = P_{cond}$. The surface velocity $v_t$ at this transition is $$v_t = \frac{\pi k}{4\rho c} \cdot \frac{\delta}{d^2},$$

and the maximum possible increase in brightness, as compared to the heat conduction limit, is equal to the ratio of $P_{cap}$ and $P_{cond}$ at the smallest possible focal spot width $\delta_{min}$, $$\frac{P_{cond}}{P_{cap}} = \frac{B_{cond}}{B_{cap}} = 8 \sqrt{\frac{\rho c}{\pi k}} \cdot \sqrt{\delta_{min} \, v}$$

Figure 17:
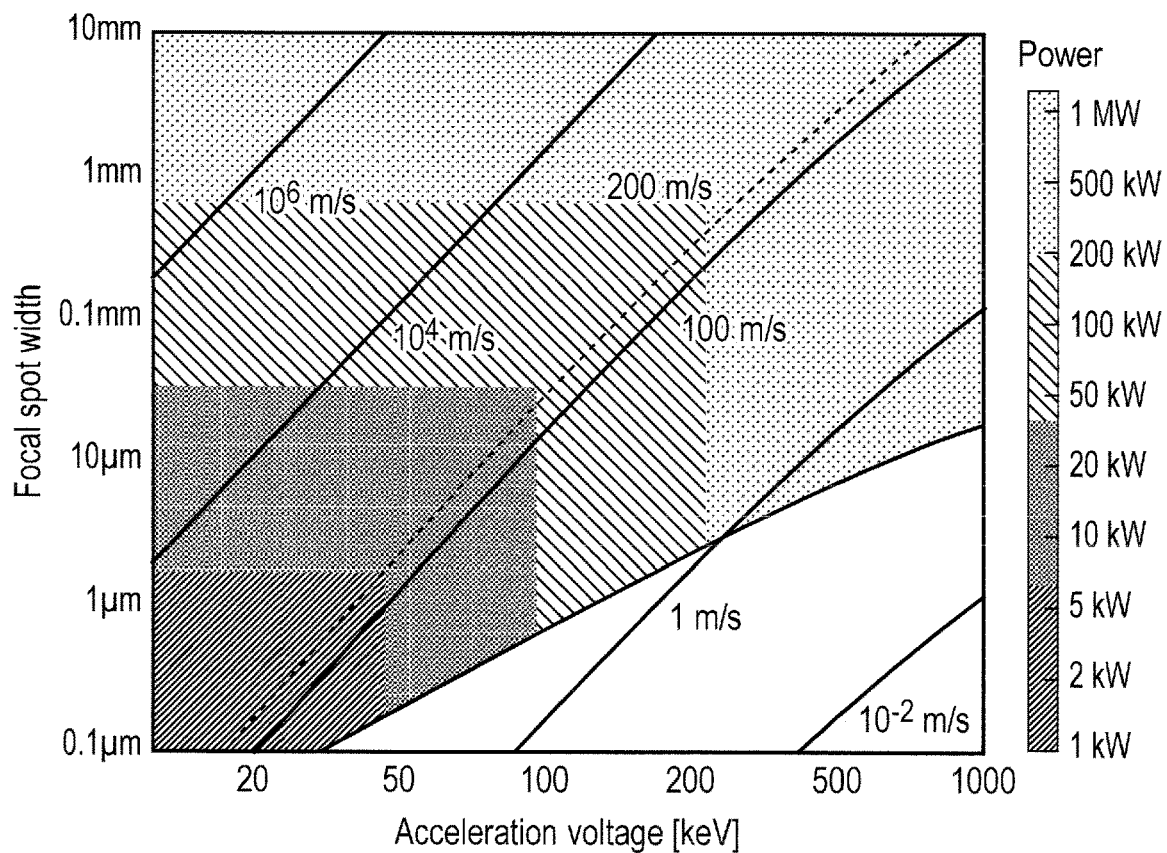
FIG. 17 shows x-ray tube performance at different focal spot widths and acceleration voltages: The maximum possible electron beam power of the x-ray tube is shown in a colour scale at a surface velocity of 200 m/s and a maximum temperature increase of 2500 K in the focal spot. The dashed line is the width-voltage contour for the transition from heat conduction limit to heat capacity limit at a surface velocity of 200 m/s, and the solid contour lines show the corresponding transitions from heat conduction limit to heat capacity limit at selected other surface velocities.

As discussed in the subsection above, anode surface velocities of up to around 200 m/s can be reached in specialized but conventional rotating anode x-ray tubes. However, velocities of up to around 1000 m/s are possible with a system of the type shown in FIG. 2. FIG. 17 shows the maximum possible power of an electron beam hitting a rotating tungsten target in a 1 cm long (h) focal spot in dependence on the focal spot width δ and the electron beam energy. The surface velocity of the anode is assumed to be v=200 m/s and the maximum temperature increase ΔT=2500 K. The contour lines show the transition from heat conduction limit to heat capacity limit at v=200 m/s and selected other surface velocities. While the maximum electron beam power at a given voltage depends on the focal spot width in the heat conduction limit, it is independent of the focal spot width at a given voltage in the heat capacity limit. However, the maximum electron beam power at a given spot width becomes energy dependent in the heat capacity limit, since it is influenced by the electron penetration depth d. A final physical lower limit for the focal spot width is given by lateral electron scattering. This is indicated by the white area at the bottom of the graph with $\delta < \delta_{min}$.

A system of the type shown in FIG. 2 operating in the heat capacity limit (hereafter termed a "line-focus tube"—LFT), not only enables the translation of several highly promising technical developments in medicine into clinical practice, but can also promote and simplify x-ray applications in various other areas where high brilliance is essential. For these applications, the system can be used with or without the collimator 212, and also can be used with or without the relative movement of the focal spot 206 along the direction 208 parallel to the cylindrical axis of the target 205. In high resolution x-ray imaging, for example, resolution is limited by the size of the source and contrast resolution is proportional to $N^{-1/2}$. The LFT facilitates the fast acquisition of high resolution 2D and 3D images.

Figure 18:
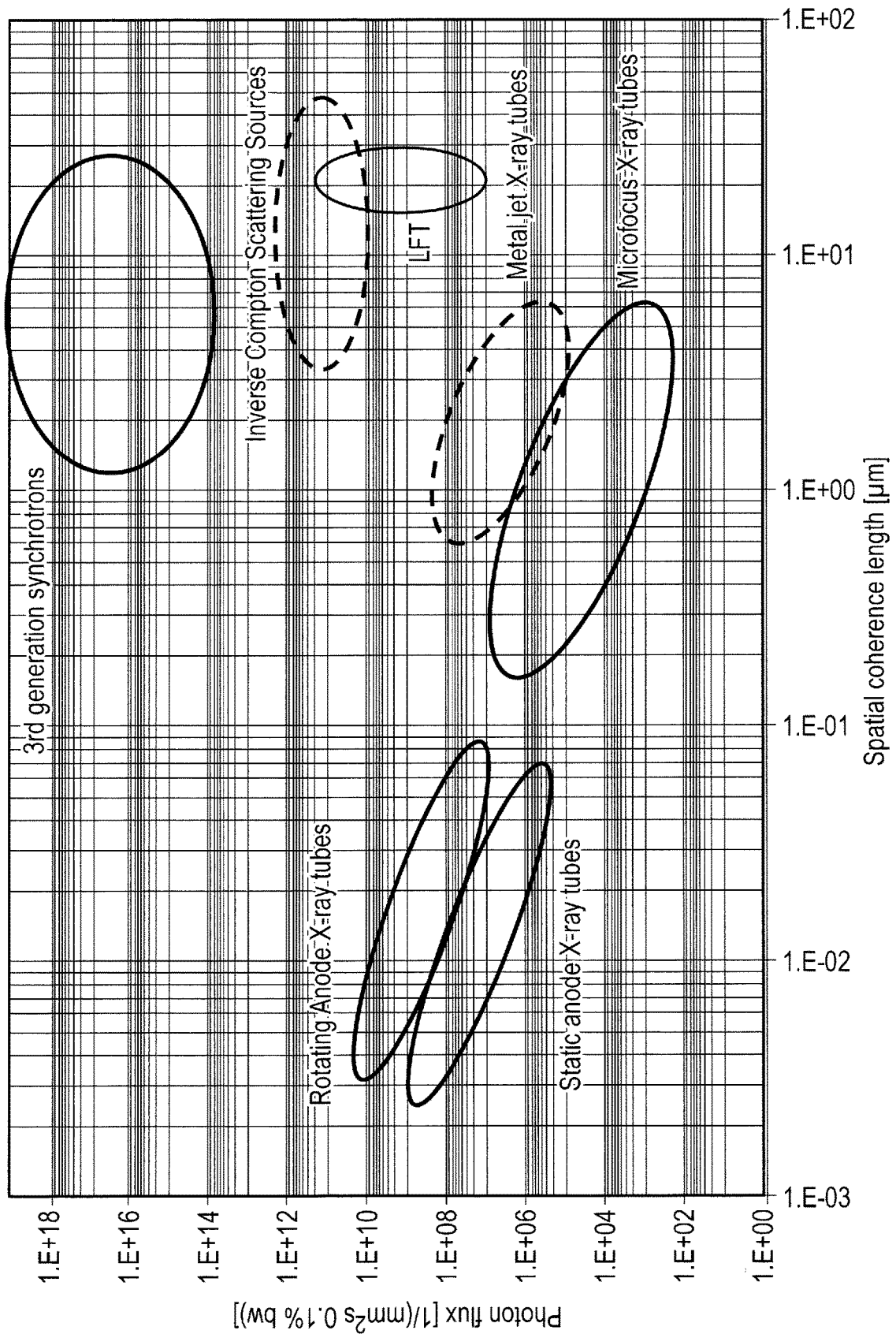
FIG. 18 shows a performance comparison of various x-ray sources: A line focus tube (LFT) according to the present invention is compared to 3rd generation synchrotrons, Inverse Compton Scattering Sources and various types of x-ray tubes at a photon energy of 60 keV. Sources shown in dashed regions usually do not reach 60 keV.

Indeed, as previously mentioned, phase contrast imaging can provide high contrast and high resolution images. However, to observe interference a coherent radiation source is needed. Conventionally suitable spatial coherence can be obtained using gratings, but these absorb a substantial part of the initial x-ray beam intensity. This can be avoided by using the LFT as a spatially coherent source in the first place whose photon flux is comparable to that of rotating anode x-ray tubes used in conventional x-ray imaging. FIG. 18 compares the various existing x-ray sources in terms of coherence lengths and photon flux, and shows that the LFT competes in photon flux and spatial coherence perpendicular to the long axis of the focal spot with Inverse Compton Scattering sources. See the Appendix for derivations of the comparison of FIG. 18.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

APPENDIX

Derivation of Heat Transport in Heat Capacity Limit

We here derive the target heating in the heat capacity limit, i.e. we assume no heat transport during the time of heating. In practice both, heat conduction and electron energy transport contribute to the heat dissipation. Especially at conditions where the heat diffusion and the electron range are of similar size, the temperature increase at the focal spot in practice is lower than calculated by either of the two models.

A volume element δV receiving over a time dt the thermal power δP increases in temperature dT according to $$\delta P dt = \rho c \delta V dT$$

Figure 19:
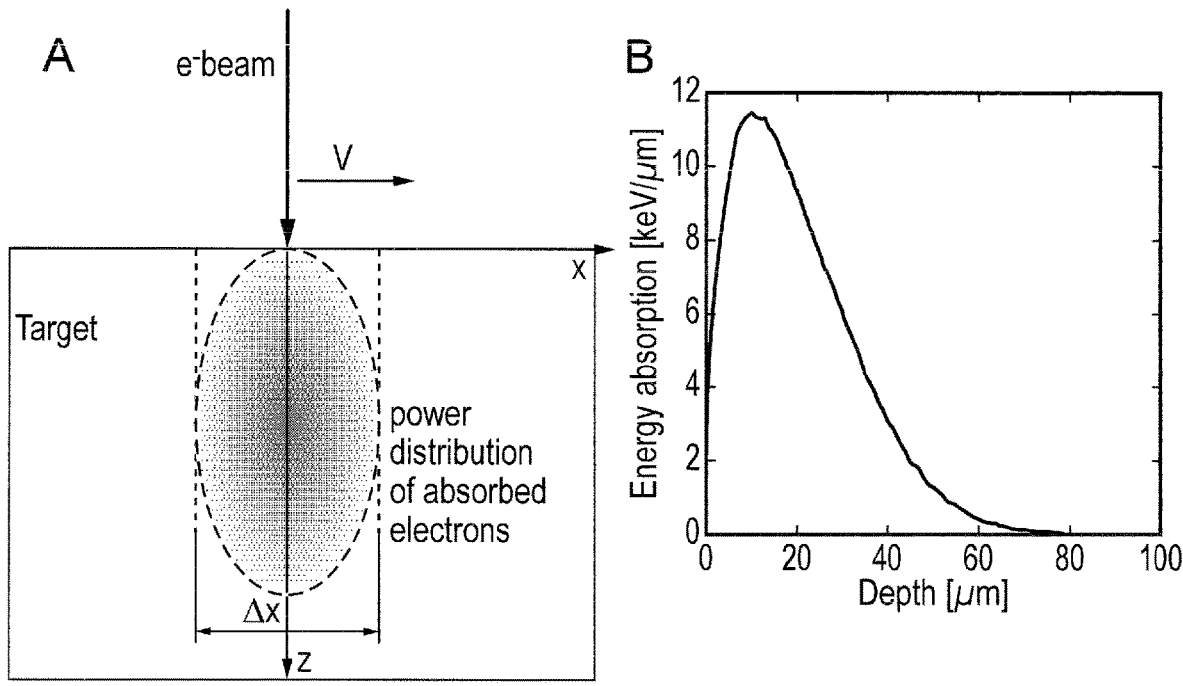
FIG. 19A shows the geometry at the anode surface for electron beam energy absorption in the target material. A thin electron beam that moves along the x-axis hits the target material and causes a power distribution in the target material.
FIG. 19B depicts the energy absorption per depth interval for a 500 keV electron beam in tungsten. The maximum of the energy absorption at around 10 μm depth can be used to calculate the electron penetration depth d.

FIG. 19A shows the geometry in the LFT. The electron beam moves with velocity v along x relative to the target surface. Electrons are statistically scattered and absorbed in the target material and create a power distribution $\delta P/\delta V(x, y, z)$. This distribution is time dependent, since the beam is moving along x, i.e. $x = x(t)$. The total temperature increase ΔT that a volume element δV experiences can be calculated via $$\int_{-\frac{\Delta t}{2}}^{\frac{\Delta t}{2}} \frac{\delta P}{\delta V}(x(t), y, z) dt = \rho c \Delta T$$

Assuming that the length h of the focal spot is much larger than the electron scattering range and that $\delta P/\delta V$ does not depend on y and $$\frac{\delta P}{\delta V}(x(t), y, z) = \frac{1}{h}\frac{\delta^2 P}{\delta x \delta z}(x(t), z) = \frac{\dot{N}_{el}}{l}\left\langle\frac{\delta^2 E_{el}}{\delta x \delta z}(x(t), z)\right\rangle.$$

We replace the power P by the number of electrons per time $N_{el}$ times the average kinetic energy absorption of an electron $E_{el}$. Integration of this expression in the previous integral leads to $$\frac{\dot{N}_{el}}{vl}\int_{-\frac{\Delta x}{2}}^{\frac{\Delta x}{2}}\frac{\delta^2 E_{el}}{\delta x \delta z}(x, z)dx = \frac{\dot{N}_{el}}{vl}\left\langle\frac{\delta E_{el}}{\delta z}(z)\right\rangle = \frac{P}{vl}\frac{1}{E_{el}}\left\langle\frac{\delta E_{el}}{\delta z}(z)\right\rangle = \rho c \Delta T$$

The maximal temperature increase is given where $$\left\langle\frac{\delta E_{el}}{\delta z}(z)\right\rangle$$

reaches its maximum and hence the quantity $$E_{el}/\left\langle\frac{\delta E_{el}}{\delta z}(z)\right\rangle_{max}$$

can be identified with the electron penetration depth d. The electron penetration depth can be calculated in Monte Carlo simulations. The following Table A1 presents values computed in the Geant4™ tool set version 10.0 p03 using the Penelope™ low energy physics libraries (https://geant4.web.cern.ch/geant4/). For electrons with a kinetic energy of 600 keV FIG. 19B shows $$\left\langle\frac{\delta E_{el}}{\delta z}\right\rangle$$

as a function of depth z.

TABLE A1

| E [keV] | 20 | 50 | 100 | 200 | 500 | 1000 |
|---|---|---|---|---|---|---|
| d [μm] | 0.322 | 1.28 | 3.99 | 11.2 | 43.7 | 107 |

Estimation of $\delta_{min}$

The achievable focal spot width depends on the possibility to focus the electrons to a focal spot with a high aspect ratio $h/\delta$, and on the scattering of the electrons in the target material.

Figure 20:
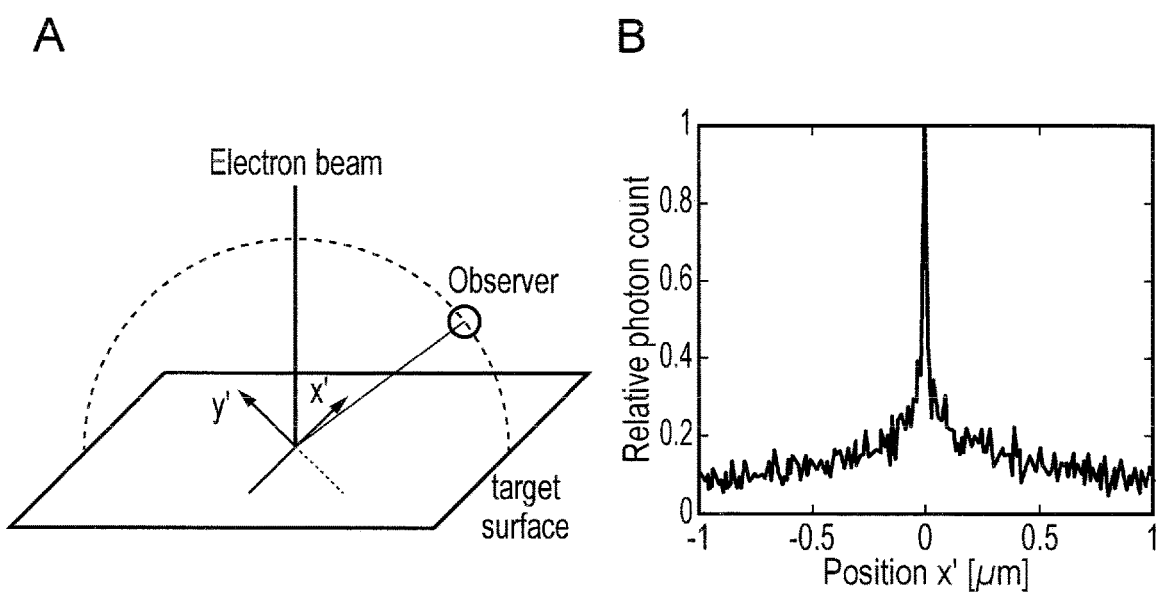
FIG. 20A shows the geometry used for a Monte Carlo study of the focal spot size in a simulation of the electron scattering limit of the focal spot width. An electron beam hits the surface of the tungsten target. At an observer position the trajectories of created photons are recorded and their origin in the x'-y' plane calculated.
FIG. 20B presents a profile of the photon origin along the x' axis.

In order to calculate the scattering limit of the focal spot size we used Geant4™ to simulate an infinitely small beam hitting a tungsten surface perpendicular in a point producing bremsstrahlung as shown in FIG. 20A. At an observer point, photon trajectories were recorded and the apparent source distribution in the x'-y' plane calculated. The result is shown in FIG. 20B for a 100 keV electron beam. The full width at half maximum (FWHM) of the source measures only between 10 and 80 nm. However, due to electron scattering there is a relatively high background noise. More conservatively the source could be defined as the width (FWHM) of the lateral electron scattering which is in the order of d/3 (e.g. 1.6 μm in tungsten for 100 keV electrons).

Estimation of Photon Fluxes and Spatial Coherences

FIG. 18 compares various sources in terms of coherence length and photon flux. The delineated performance regions are only a rough estimate, though based on data of typical existing sources.

Figure 21:
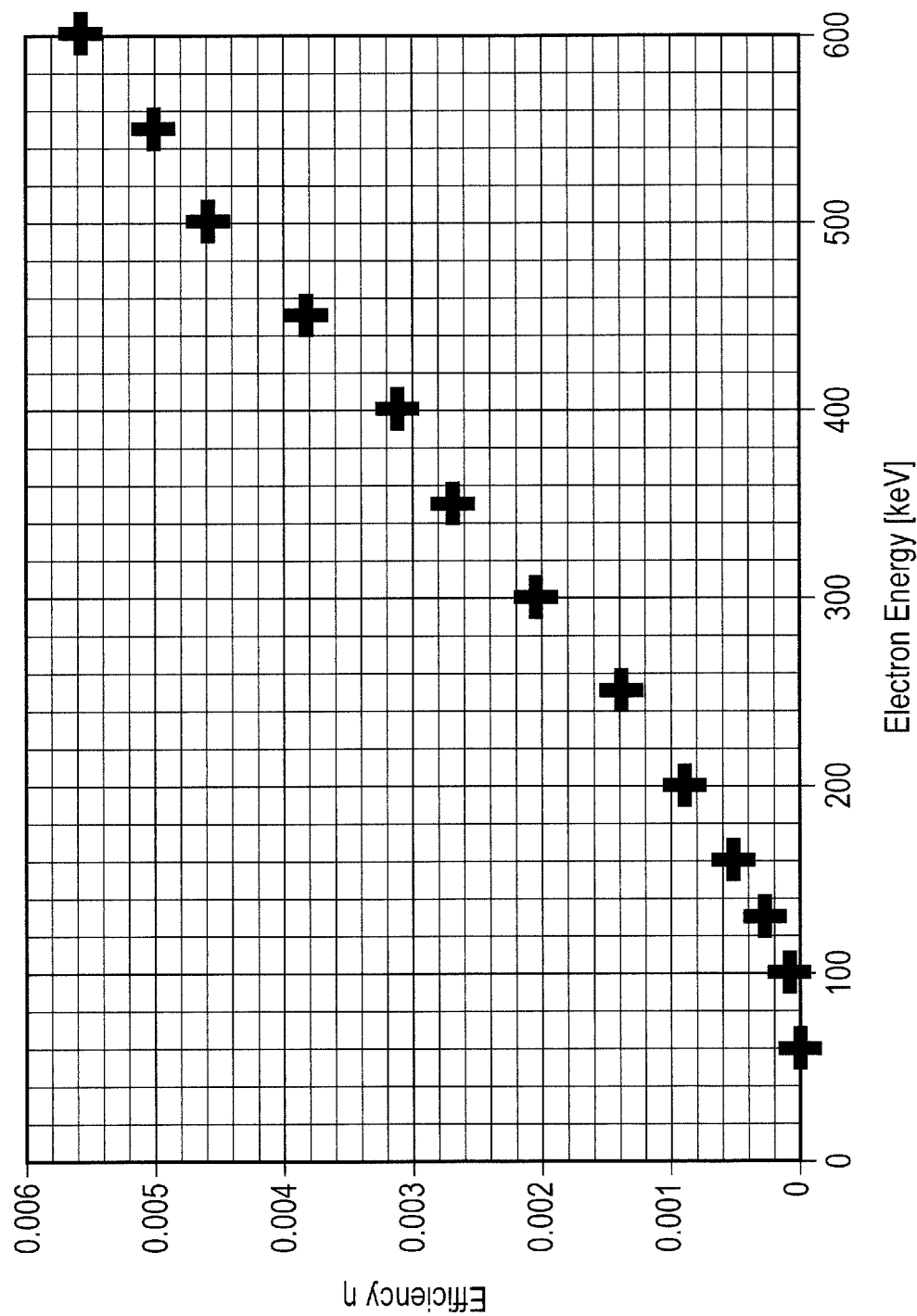
FIG. 21 shows efficiency of electron to photon conversion in a tungsten target. The conversion efficiency is defined as the number of photons at the tungsten Kα1 fluorescence line emitted per electron. It is zero below and strongly increasing with electron energy above 59.3 keV.

The performance of the x-ray tubes was estimated at the Kα1 absorption edge of tungsten, i.e. at a photon energy of 59.3 keV and a wavelength $\Delta$ of 20.7 μm. The distance r from the source was assumed to be 1 m. For a source with random phase distributions, the spatial coherence length $l_s$ can be approximated by $$l_s = \lambda \cdot \frac{r}{\delta},$$

where $\delta$ is the source diameter. The flux at distance r, x-ray tube power P and acceleration voltage U can be calculated from $$\Phi = \eta \frac{P}{eU} f_{\Delta\Omega} \cdot \frac{1}{r^2},$$

where e denotes the electron charge, $\eta$ the electron conversion efficiency as the number of Kα1 fluorescence photons per electron and $f_{\Delta\Omega}$ is the fraction of photons emitted in a certain angle interval. The electron conversion efficiency strongly increases with acceleration voltage U for U>59.3 keV and was calculated in Monte Carlo simulations in Geant4™ at various electron energies as shown in FIG. 21. The fraction of photons emitted per angle interval resembles a completely isotropic source, $$f \approx 2 \cdot 10^{-7} mrad^{-2}.$$

The parameters $\eta$ and $f_{\Delta\Omega}$ are the same for all x-ray tubes with a tungsten target. Only P, U and the focal spot size vary.

A Varian HPX-160-11 stationary anode x-ray tube with U=160 kV a focal spot size of 0.4 mm at 800 W or 1.0 mm at 1800 W is an example of a conventional x-ray tube. This leads to a coherence length of 51.8 nm and 20.7 nm and a photon flux of $3.25 \cdot 10^6$ mm$^{-2}$ s$^{-1}$ and $7.32 \cdot 10^6$ mm$^{-2}$ s$^{-1}$ at the small and large focal spot size, respectively.

A typical rotating anode tube is the Siemens™ Straton Tube with U=140 kV, P=100 kW and a focal spot size of 1.8×7.2 mm. This leads to a coherence length $l_s$ of 15 nm in 1 m distance from the source and a photon flux of around $2.8 \cdot 10^8$ mm$^{-2}$ s$^{-1}$. (Oppelt et al., ibid.)

Microfocus tubes typically operate at an electron beam power of 4-40 W, (e.g. Hamamatsu™ microfocus x-ray tube series) at focal spot sizes between 5 and 80 μm with acceleration voltages between 20 and 160 kV. The coherence length is in the order of 0.2 to 5.0 μm and the photon flux will be between $2 \cdot 10^4$ and $2 \cdot 10^5$ mm$^{-2}$ s$^{-1}$.

Metal jet x-ray tubes employ other target materials and therefore the conversion efficiency and the fluorescence lines are different. As an example is Excillum™ metal jet x-ray tubes. The brilliance is reported to be between $2.6 \cdot 10^{10}$ and $10 \cdot 10^{10}$ $$\frac{1}{s \, mm^2 mrad^2}$$

per spectral line and the source size between 5 and 20 μm. At 5 μm focal spot size the flux is between $6.5 \cdot 10^5$ and $2.5 \cdot 10^6$ mm$^{-2}$ s$^{-1}$. Unfortunately metal jet x-ray tubes operate at lower photon energies. However, to compare coherence lengths a wavelength of 20.7 μm can be assumed, which leads to a coherence length of around 4 μm.

For the inverse Compton Scattering source at the Massachusetts Institute of Technology a beam brilliance of $2 \cdot 10^{15}$ $$\frac{1}{s\ mm^2 mrad^2 0.1\%bw}$$

and a source size of 2 times 6 μm are reported (Graves W, Brown W, Kaertner F, Moncton D. *MIT inverse Compton source concept*. Nuclear Instruments and Methods in Physics Research Section A: Accelerators, Spectrometers, Detectors and Associated Equipment. 2009; 608(1):5103-55). At a source distance of again 1 m this infers a photon flux of $2.4 \cdot 10^{10}$ mm$^{-2}$ s$^{-1}$ at a coherence length of 3 to 10 μm.

The best performance is achieved by 3$^{rd}$ generation synchrotrons with a brilliance between $10^{20}$ and $10^{24}$ $$\frac{1}{s\ mm^2 mrad^2 0.1\%bw}$$

(Huang Z. *Brightness and coherence of synchrotron radiation and FELs*. MOYCB101, Proceedings of IPAC 2013, Shanghai, China. 2013) and a source diameter of around 50 μm (e.g. Lengeler B, Schroer C G, Kuhlmann M, Benner B, Günzler T F, Kurapova O, et al. *Refractive x-ray lenses*. Journal of Physics D: Applied Physics. 2005; 38(10A): A218). The distance between source and experiment is usually much larger than 1 m. Therefore we assume, deviating from the previous estimates, a source distance r of 40 m. There the flux is between $10^{14}$ and $10^{18}$ mm$^{-2}$ s$^{-1}$ and the coherence length around 15 μm at a photon energy of 60 keV.

The invention claimed is:

1. An x-ray micro-beam radiation production system having:
   a source of accelerated electrons;
   an electron focusing component configured to focus the electrons provided by the source;
   a target which produces x-rays when electrons impinge thereon from the source; and
   a collimator having one or more micro-beam forming apertures which collimate the produced x-rays into one or more respective micro-beams, the, or each, micro-beam forming aperture having a given shape on a cross-section therethrough perpendicular to the formed micro-beam;
   wherein the electron focusing component is configured to focus the electrons provided by the source such that they impinge at a focal spot formed on a surface of the target, the focal spot having substantially the same shape as a projection of the cross-sectional shape of the aperture(s) onto the target surface at the focal spot such that partial shadowing of the source along the micro-beam path behind the collimator is avoided;
   wherein the target is movable relative to the focusing component such that the focal spot moves across the target surface; and
   wherein at a distance of 500 mm from the target, the one or more micro-beams formed by the collimator deliver a dose rate of at least 1 Gy/s.

2. The system of claim 1, wherein the target is cylindrical, and the target rotates around its axis to move the target surface relative to the focusing component.

3. The system of claim 2, wherein the target rotates to provide a speed of movement of the focal spot over the surface of the target of at least 50 m/s.

4. The system of claim 1, wherein the, or each, aperture in the collimator is a slit, and the focal spot is correspondingly elongate in shape, the length direction of the slit(s) and the length direction of the elongate focal spot being parallel.

5. The system of claim 4, wherein the cross-sectional shape of the, or each, micro-beam forming aperture is rectangular.

6. The system of claim 4, wherein the shortest dimension of the elongate focal spot is less than 1 mm in width.

7. The system of claim 4, wherein the cross-section of the, or each, slit has a width of from 20 μm to 500 μm.

8. The system of claim 1, wherein there are plural apertures, and the centre-to-centre distance between adjacent apertures is from 100 μm to 4000 μm.

9. The system of claim 1, wherein the electrons impinge on the target surface at a target angle, and wherein the target angle is controlled by the focusing component to be no more than 20° from the normal to the target surface at the focal spot.

10. The system of claim 1, wherein the electrons are accelerated with an acceleration voltage of at least 100 kV.

11. A method of operating the system of claim 1, having the steps of:
   moving the target relative to the focusing component;
   providing electrons from the electron source;
   focusing the electrons using the electron focusing component such that they impinge at a focal spot formed on the surface of the target, thereby producing x-rays; and
   collimating the resulting x-rays using the collimator thereby producing one or more x-ray micro-beams;
   wherein the focal spot has substantially the same shape as a projection of the cross-sectional shape of the aperture(s) onto the target surface at the focal spot such that partial shadowing of the source along the micro-beam path behind the collimator is avoided; and
   wherein at a distance of 500 mm from the target, the one or more micro-beams formed by the collimator deliver a dose rate of at least 1 Gy/s.

12. The method of claim 11, wherein the, or each, micro-beam produced by the collimator has a beam width of from 20 to 500 μm.

13. The method of claim 11, wherein at a distance of 500 mm from the target the micro-beam(s) formed by the collimator deliver a radiation dose rate of up to 1200 Gy/s.

14. The method of claim 11, wherein the provided electrons are accelerated with an acceleration voltage of at least 100 kV.

* * * * *